US012624048B2

(12) United States Patent
Miyazaki et al.

(10) Patent No.: US 12,624,048 B2
(45) Date of Patent: May 12, 2026

(54) PHOTOCHROMIC CYCLIC COMPOUND AND CURABLE COMPOSITION CONTAINING THE PHOTOCHROMIC CYCLIC COMPOUND

(71) Applicant: TOKUYAMA CORPORATION, Shunan (JP)

(72) Inventors: Masayuki Miyazaki, Shunan (JP); Junji Takenaka, Shunan (JP); Junji Momoda, Shunan (JP); Srinivas Venu, Shunan (JP); Katsuhiro Mori, Shunan (JP)

(73) Assignee: TOKUYAMA CORPORATION, Shunan (JP)

( * ) Notice: Subject to any disclaimer, the term of this patent is extended or adjusted under 35 U.S.C. 154(b) by 890 days.

(21) Appl. No.: 17/798,597

(22) PCT Filed: Feb. 18, 2021

(86) PCT No.: PCT/JP2021/006218

§ 371 (c)(1),
(2) Date: Aug. 10, 2022

(87) PCT Pub. No.: WO2021/167027

PCT Pub. Date: Aug. 26, 2021

(65) Prior Publication Data

US 2023/0133211 A1 May 4, 2023

(30) Foreign Application Priority Data

Feb. 18, 2020 (JP) ................................ 2020-025057
Feb. 27, 2020 (JP) ................................ 2020-031674

(51) Int. Cl.

| | |
|---|---|
| ***C07D 493/10*** | (2006.01) |
| ***C07D 497/10*** | (2006.01) |
| ***C07D 497/20*** | (2006.01) |
| ***C07D 498/10*** | (2006.01) |
| ***C07D 498/22*** | (2006.01) |
| ***C07F 7/18*** | (2006.01) |
| ***C08K 5/159*** | (2006.01) |
| ***C08K 5/549*** | (2006.01) |
| ***G02B 5/23*** | (2006.01) |

(52) U.S. Cl.

CPC ......... *C07D 493/10* (2013.01); *C07D 497/10* (2013.01); *C07D 497/20* (2013.01); *C07D 498/10* (2013.01); *C07D 498/22* (2013.01); *C07F 7/1804* (2013.01); *C08K 5/159* (2013.01); *C08K 5/549* (2013.01); *G02B 5/23* (2013.01)

(58) Field of Classification Search

CPC .. C07D 493/10; C07D 497/10; C07D 497/20; C07D 498/10; C07D 498/22; C07F 7/1804

See application file for complete search history.

(56) References Cited

U.S. PATENT DOCUMENTS

| | | | |
|---|---|---|---|
| 4,826,977 | A | 5/1989 | Heller et al. |
| 2012/0170098 | A1 | 7/2012 | Takahashi et al. |
| 2015/0368552 | A1 | 12/2015 | Izumi et al. |
| 2018/0030341 | A1 | 2/2018 | Shimizu et al. |
| 2020/0148856 | A1 | 5/2020 | Kasori et al. |
| 2020/0172681 | A1 | 6/2020 | Takenaka et al. |
| 2020/0190106 | A1 | 6/2020 | Miyazaki et al. |

FOREIGN PATENT DOCUMENTS

| | | | | |
|---|---|---|---|---|
| CN | 87 1 04184 | A | 6/1988 | |
| CN | 102471304 | A | 5/2012 | |
| CN | 110799573 | A | 2/2020 | |
| CN | 111718706 | A * | 9/2020 | ........... C07F 7/1804 |
| JP | 52-46079 | A | 4/1977 | |
| JP | 63-86178 | A | 3/1988 | |
| JP | 4-112885 | A | 4/1992 | |
| JP | 6-199827 | A | 7/1994 | |
| JP | 8-217985 | A | 8/1996 | |
| JP | 8-219285 | A | 11/1996 | |
| JP | 2018-62496 | A | 4/2018 | |
| JP | 2019-182866 | A | 10/2019 | |
| WO | WO 98/14443 | A1 | 4/1998 | |
| WO | WO 00/15629 | A1 | 3/2000 | |
| WO | WO 2014/136919 | A1 | 9/2014 | |
| WO | WO 2016/143910 | A1 | 9/2016 | |
| WO | WO 2019/009230 | A1 | 1/2019 | |

(Continued)

OTHER PUBLICATIONS

Chemical Abstracts Registry No. 183540-92-3, indexed in the Registry file on STN CAS Online Nov. 28, 1996. (Year: 1996).*
Chinese Office Action and Search Report for corresponding Chinese Application No. 202180015122.6, dated May 25, 2023, with a partial English translation.
Extended European Search Report for corresponding European Application No. 21757643.8, dated Feb. 26, 2024.
Coelho et al., "The effect of a sulphur bridge on the photochromic properties of indeno-fused naphthopyrans", Tetrahedron, 2004, vol. 60, pp. 2593-2599.

(Continued)

*Primary Examiner* — Laura L Stockton
(74) *Attorney, Agent, or Firm* — Birch, Stewart, Kolasch & Birch, LLP

(57) ABSTRACT

The photochromic cyclic compound of the present invention is represented by Formula (1) below:

[CF 1]

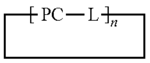

(1)

in the formula, L is a divalent bridging group and PC is a divalent T-type photochromic basic structural group having a naphthopyran structure, where one end of the bridging group L is bonded to at least the 3-position of the naphthopyran structure.

12 Claims, 1 Drawing Sheet

(56) References Cited

FOREIGN PATENT DOCUMENTS

| | | | |
|---|---|---|---|
| WO | WO 2019/013249 | A1 | 1/2019 |
| WO | WO 2019/228604 | A1 | 12/2019 |
| WO | WO 2019/238495 | A1 | 12/2019 |
| WO | WO 2020/017610 | A1 | 1/2020 |

OTHER PUBLICATIONS

International Search Report (PCT/ISA/210), issued in PCT/JP2021/006218, mailed Apr. 13, 2021.

English translation of the Japanese Office Action for corresponding Japanese Application No. 2022-501988, dated Nov. 19, 2024.

* cited by examiner

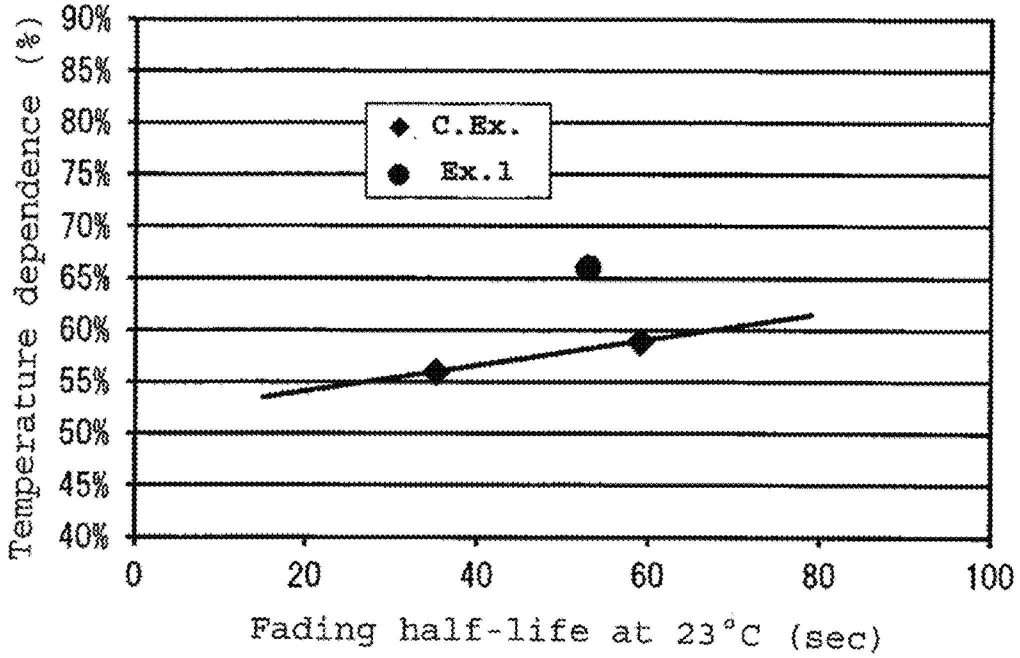
C.Ex.:Comparative Example
Ex.1: Example 1

PHOTOCHROMIC CYCLIC COMPOUND AND CURABLE COMPOSITION CONTAINING THE PHOTOCHROMIC CYCLIC COMPOUND

TECHNICAL FIELD

The present invention relates to a novel photochromic cyclic compound. More specifically, the present invention relates to novel photochromic cyclic compound with improved temperature dependence.

BACKGROUND ART

Photochromic compounds are compounds that can undergo a reversible transformation between two isomers with different absorption spectra when irradiated with ultra-violet-containing light such as sunlight or light from a mercury lamp. Usually, when a colorless compound in a decolored state is irradiated with ultraviolet rays, it rapidly undergoes isomerization (color development reaction) involving a color change to a colored compound in a color developed state. Upon isomerization from the color developed state to the decolored state (fading reaction), some photochromic compounds return to the original colorless state not only by light with a specific wavelength but also by heat. Such photochromic compounds are referred to as T-type photochromic compounds, which have been well studied and developed especially as a photochromic lens material.

Such a T-type photochromic compound to be used for a photochromic lens is usually required to possess the following properties.

(1) The degree of coloration (initial coloration) in a visible light region before ultraviolet irradiation is low.

(2) The color optical density is saturated quickly after the start of ultraviolet irradiation, that is, color development sensitivity is high.

(3) The speed (fading rate) of return to the original state after the stop of ultraviolet irradiation is high.

(4) The durability against the repetition of this reversible action is favorable.

(5) The dissolubility in a monomer composition that will serve as a host material after curing is high to achieve high dispersibility in the host material to be used.

A number of chromene compounds including naphthopyran have been studied as T-type photochromic compounds satisfying these properties.

Furthermore, since the demand for the T-type photochromic compounds has been increasing in recent years, the T-type photochromic compounds are expected to satisfy further properties that have not been requested.

In general, T-type photochromic compounds are known to have a trade-off relationship between the fading rate and the color optical density. As a result, for instance, when a T-type photochromic compound is used under high temperature as in summer with the hot sun, it is subject to fading and declines in color optical density. In other words, the compounds are easily affected by ambient environmental temperature (have large temperature dependence). In order to prevent decrease in the color optical density, a larger amount of T-type photochromic compound may be blended, so that the color optical density is increased, thereby obtaining a photochromic lens having high color optical density even under high temperature. However, as the blending amount increases, a proportional relationship between the blending amount and the color optical density usually collapses. And this countermeasure can cause other problems in cost and the dissolubility of the T-type photochromic compound itself due to the increased blending amount. That is, there is a limit to enhance the color optical density by increasing the blending amount.

As described above, a sufficient improvement has not yet been made in T-type photochromic compounds for use under high temperature as in summer by merely increasing the blending amount thereof. Under the circumstances, there has been a growing demand especially for the development of a T-type photochromic compound having high color optical density (that is, a small temperature dependence) even under high temperature as in summer.

In order to achieve a T-type photochromic compound having a high color optical density under high temperature, it is necessary to improve the thermal stability in the colored state. However, this causes a decrease in the fading rate because of the trade-off relationship between the fading rate and the color optical density. In conclusion, it is usually difficult to achieve both a fast fading rate and small temperature dependence.

In order to solve this problem, the present inventors propose a chromene compound having substituents at specific positions (see Patent Document 1). This compound has relatively small temperature dependence.

PRIOR ART DOCUMENTS

Patent Documents

Patent Document 1: JP 2018-062496

SUMMARY OF THE INVENTION

Problem to be Solved by the Invention

However, the chromene compound described in Patent Document 1 still needs improvement since the compound has a substituent at a specific position, namely, the color tone may be limited. In general, chromene compounds are designed to satisfy desired photochromic properties for their purposes by various substituents. Though it is possible to achieve a chromene compound with smaller temperature dependence by limiting the substituents according to the technique of Patent Document 1, it is difficult to impart photochromic properties (i.e., color tone) for satisfying all of the remaining properties.

Means for Solving the Problems

In view of the aforementioned situation, the present inventors have studied various structures, substituents, positions of the substituents, and combinations of substituents. As a result, the inventors have found that it is possible to improve the temperature dependence by forming a cyclic structure by bonding a 3-position of the naphthopyran skeleton that exhibits the T-type photochromic properties to a specific bridging group, thereby completing the present invention.

According to the present invention, a photochromic cyclic compound represented by Formula (1) below is provided:

[CF 1]

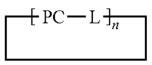

(1)

in the formula,

PC denotes a divalent T-type photochromic basic structural group, L denotes a divalent bridging group, and n is an integer of 1 or more, the PC to denote the T-type photochromic basic structural group is a naphthopyran structural group represented by Formula (2) below:

[CF 2]

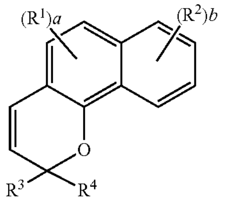

(2)

In Formula (2), provided that at least one of $R^3$ and $R^4$ is a bonding hand to the divalent bridging group L or a group having the bonding hand, $R^1$ and $R^2$ are each a group having a bonding hand to the divalent bridging group L or a group having the bonding hand, a hydroxyl group, an alkyl group, a cycloalkyl group, an alkoxy group, an amino group, a heterocyclic group, a cyano group, a halogen atom, an alkylthio group, an arylthio group, a nitro group, a formyl group, a hydroxycarbonyl group, an alkylcarbonyl group, an alkoxycarbonyl group, an aralkyl group, an aralkoxy group, an aryloxy group, an aryl group, a heteroaryl group, a thiol group, an alkoxyalkylthio group, a cycloalkylthio group, or a group represented by Formula (X) below:

[CF 3]

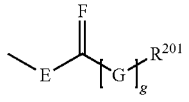

(X)

(in the formula,

E is an oxygen atom or $NR^{101}$, and $R^{101}$ is a hydrogen atom or an alkyl group, F is an oxygen atom or a sulfur atom, G is an oxygen atom, a sulfur atom or a $NR^{202}$, and $R^{202}$ is a hydrogen atom, an alkyl group, a cycloalkyl group, an aryl group or a heteroaryl group, g is an integer of 0 or 1, $R^{201}$ is a hydrogen atom, an alkyl group, a cycloalkyl group, an aryl group or a heteroaryl group, in a case where G is an oxygen atom or a sulfur atom, $R^{201}$ is a group other than a hydrogen atom), or a group represented by Formula (Y) below:

[CF 4]

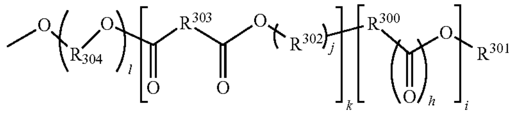

(Y)

(in the formula, $R^{300}$ is an alkylene group, or a silylene group having as a substituent an alkyl group or an aryl group, $R^{301}$ is an alkyl group or an aryl group, $R^{302}$, $R^{303}$ and $R^{304}$ are alkylene groups, h, j, k and l are integers of 0 or 1, i is an integer of 2 to 200, and the plural i may be expressed in the same or different units), $R^1$ and $R^2$ may together form a ring that may have a heteroatom, a is an integer of 0 to 2, and b is an integer of 0 to 4, when a is 2, two $R^1$ may be different from each other, and in a case where a is 2 and two $R^1$ are present adjacent to each other, the two $R^1$ may together form a ring that may have a heteroatom, in a case where b is 2 to 4, a plurality of $R^2$ may be different from each other, and in a case where b is 2 to 4 and two $R^2$ are present adjacent to each other, the adjacent $R^2$ may together form a ring that may have a heteroatom, $R^3$ and $R^4$ are each a bonding hand to the divalent bridging group L or a group having the bonding hand, an aryl group or a heteroaryl group, and the divalent bridging group L is a group represented by Formula (3) below:

[CF 5]

$$—R^8\text{-}R^9—R^{10}— \quad (3)$$

in Formula (3), provided that not all of $R^8$, $R^9$ and $R^{10}$ become direct bonds at the same time, $R^8$ and $R^{10}$ are each either a direct bonding hand or a divalent aromatic ring group having 6 to 30 carbon atoms, and $R^9$ is a direct bonding hand or a divalent organic group.

In the photochromic cyclic compound of the present invention, the following embodiments can be adopted.

(1) The n in Formula (1) is an integer of 2 or more. (In other words, at least two basic structural groups PC for exhibiting photochromic properties are present in the ring.)

(2) The naphthopyran structural group is an indenonaphthopyran structural group represented by Formula (4) below:

[CF 6]

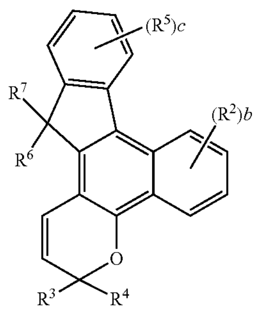

(4)

in the formula, $R^2$, $R^3$, $R^4$ and b are as described above, a structural moiety in which ($R^5$) c, $R^6$ and $R^7$ are present is a cyclic moiety formed with two $R^4$ in Formula (2), $R^5$ is a bonding hand to a divalent bridging group L, a hydroxyl group, an alkyl group, a cycloalkyl group, an alkoxy group, an amino group, a heterocyclic group, a cyano group, a halogen atom, an alkylthio group, an arylthio group, a nitro group, a formyl group, a hydroxycarbonyl group, an alkylcarbonyl group, an alkoxycarbonyl group, an aralkyl group, an aralkoxy group, an aryloxy group, an aryl group, a heteroaryl group, a thiol group, an alkoxyalkylthio group, a cycloalkylthio group, the Formula (X), or the Formula (Y), c is an integer of 0 to 4, in a case where c is 2 to 4, a plurality of $R^5$ may be different from each other, and in a case where c is 2 to 4 and two $R^5$ are present adjacent to each other, the two $R^5$ may together form a ring that may contain a heteroatom, $R^6$ and $R^7$ are each a bonding hand to the divalent bridging group L, a hydrogen atom, a hydroxyl group, an alkyl group, a cycloalkyl group, an alkoxy group, an alkoxyalkyl group, a formyl group, a hydroxycarbonyl group, an alkylcarbonyl group, an alkoxycarbonyl group, a halogen atom, an aralkyl group, an aralkoxy group, an aryloxy group, an aryl group, a heterocyclic group, the Formula (X), or the Formula (Y), and $R^6$ and $R^7$ may together form an aliphatic ring having 3 to 20 membered carbon atoms, a fused polycyclic ring in which an aromatic ring or an aromatic heterocyclic ring is fused with the aliphatic ring, a heterocyclic ring having 3 to 20 membered carbon atoms, or a fused polycyclic ring in which an aromatic ring or an aromatic heterocyclic ring is fused with the heterocyclic ring.

(3) In the indenonaphthopyran structural group represented by the Formula (4), a ring formed of a combination of $R^6$ and $R^7$ is any one selected from the group consisting of:

an aliphatic ring having 3 to 20 membered carbon atoms;

a fused polycyclic ring in which an aromatic ring or an aromatic heterocyclic ring is fused with the aliphatic ring;

a heterocyclic ring having 3 to 20 membered carbon atoms; or a fused polycyclic ring in which an aromatic ring or an aromatic heterocyclic ring is fused with the heterocyclic ring.

(4) In the ring formed of the combination of $R^6$ and $R^7$, the aliphatic ring having 3 to 20 carbon atoms is selected from the group consisting of a cyclopentane ring, a cyclohexane ring, a cycloheptane ring, a cyclooctane ring, a cyclononane ring, a cyclodecane ring, a cycloundecane ring, a cyclododecane ring, and a spirodicyclohexane ring.

(5) The aliphatic ring has 1 to 10 substituents, the substituent being an alkyl group having 1 to 3 carbon atoms or a cycloalkyl group having 5 to 7 carbon atoms, or the aliphatic ring is a ring with which a cycloalkyl group having 5 to 7 carbon atoms is fused.

(6) $R^3$ and $R^4$ in Formula (2) are bonded to the divalent bridging group L.

(7) The divalent bridging group L has a molecular weight of less than 1000.

The present invention provides also a photochromic curable composition comprising the aforementioned photochromic cyclic compound and a polymerizable compound, and further provides a photochromic optical article formed by polymerizing the photochromic curable composition.

The present invention further provides a polymer molded body in which the aforementioned photochromic cyclic compound is dispersed inside, and provides also an optical article coated with a polymer film in which the aforementioned photochromic cyclic compound is dispersed.

Effect of the Invention

As for the photochromic cyclic compound of the present invention, a divalent T-type photochromic basic structural group PC (that is, a photochromic moiety) contained in the molecules is a naphthopyran structural group. A specific divalent bridging group is bonded to the 3-position of such a naphthopyran structural group so as to forma cyclic structure. The cyclic structure includes one or at least two photochromic basic structural group(s) PC. This cyclic structure enables to decrease the temperature dependence in comparison with a photochromic compound including no naphthopyran structural group in the cyclic structure. Although the detail of why such an effect is obtained is unknown, the present inventors consider it as follows.

That is, since a divalent bridging group is bonded to at least one of the groups at 3-positions of at least one naphthopyran thereby forming a cyclic structure, the molecular motions may be limited. That is, as compared with the case of naphthopyran which is not bonded to a cyclic structure, the molecular motion is restricted, so that fading tends to occur. It is considered that fading will occur easily without changing the thermal stability of the naphthopyran, and it is presumed that even in a high temperature state, a color development state can be maintained and a temperature dependence can be lowered compared with individual cases.

As described above, it is considered that the photochromic cyclic compound of the present invention is not exhibited by a specific substituent (a specific type, a group which is substituted at a specific position), but is generated as a result of restricting the motion of any one of the groups at least at the 3-position of the at least one naphthopyran. Therefore, since it does not depend on a specific substituent or the like affecting the color tone, there may be a low possibility that the color tone is limited.

Therefore, in a case where the photochromic cyclic compound of the present invention is used for manufacturing a photochromic lens for instance, a photochromic lens having a small temperature dependence and a high color optical density even under high temperature as in summer can be made.

BRIEF DESCRIPTION OF THE DRAWINGS

FIGURE: a chart showing relationships between temperature dependence and a fading half-life of compounds in Examples and Comparative Examples.

MODE FOR CARRYING OUT THE INVENTION

<Photochromic Cyclic Compound>

The photochromic cyclic compound of the present invention is represented by Formula (1) below.

[CF 7]

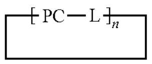

(1)

In Formula (1), PC denotes a divalent T-type photochromic basic structural group, L denotes a divalent bridging group, and n is an integer of 1 or more.

The T-type photochromic basic structural group is a naphthopyran structural group having a naphthopyran skeleton as a photochromic moiety, and the photochromic cyclic compound of the present invention has a cyclic structure formed by bonding a divalent bridging group directly or via a predetermined group at least at the 3-position of the naphthopyran structural group. Since the structure includes one or at least two photochromic moieties, the molecular motion can be easily restricted. As a result, a photochromic cyclic compound having a small temperature dependence and excellent color development at high temperature can be obtained.

The photochromic cyclic compound of the present invention represented by Formula (1) has various groups and rings. Any known substituents that do not inhibit photochromic properties may be introduced unless otherwise specified. For instance, a halogen atom, an OH group or the like may be introduced into an alkyl group. This holds true for an aliphatic ring or an aromatic ring heterocycle.

In the present invention, the naphthopyran structural group (group PC) is represented by Formula (2) below.

[CF 8]

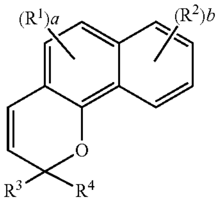

(2)

In Formula (2), a is an integer of 0 to 2, and b is an integer of 0 to 4. $R^1$-$R^4$ each indicates the following group for instance, provided that at least either $R^3$ or $R^4$ is a bonding hand to the divalent bridging group L or a group having the bonding hand.

Examples of $R^1$ and $R^2$ are as follows:

a bonding hand to the divalent bridging group L or a group having the bonding hand;

a hydroxyl group;

an alkyl group (especially one having 1 to 6 carbon atoms);

a cycloalkyl group (especially one having 3 to 8 carbon atoms);

an alkoxy group (especially one having 1 to 6 carbon atoms);

an amino group;

a heterocyclic group;

a cyano group;

a halogen atom;

an alkylthio group;

an arylthio group;

a nitro group;

a formyl group;

a hydroxycarbonyl group;

an alkylcarbonyl group (especially one having 2 to 7 carbon atoms);

an alkoxycarbonyl group (especially one having 2 to 7 carbon atoms);

an aralkyl group (especially one having 7 to 11 carbon atoms);

an aralkoxy group (especially one having 7 to 11 carbon atoms);

an aryloxy group (especially one having 6 to 12 carbon atoms);

an aryl group (especially one having 6 to 12 carbon atoms);

a heteroaryl group;

a thiol group;

an alkoxyalkylthio group (especially one having 3 to 8 carbon atoms);

a cycloalkylthio group (especially one having 3 to 8 carbon atoms); or a group represented by Formula (X) below.

[CF 9]

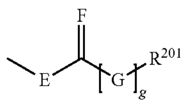

(X)

(in the formula,

E is an oxygen atom or $NR^{101}$, and $R^{101}$ is a hydrogen atom or an alkyl group, F is an oxygen atom or a sulfur atom, G is an oxygen atom, a sulfur atom or a $NR^{202}$, and $R^{202}$ is a hydrogen atom, an alkyl group, a cycloalkyl group, an aryl group or a heteroaryl group, g is an integer of 0 or 1, $R^{201}$ is a hydrogen atom, an alkyl group, a cycloalkyl group, an aryl group or a heteroaryl group, and in a case where G is an oxygen atom or a sulfur atom, $R^{201}$ is a group other than a hydrogen atom), and a group represented by Formula (Y) below:

[CF 10]

(Y)

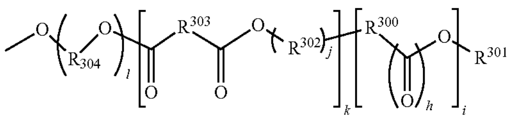

(in the formula, $R^{300}$ is an alkylene group or a silylene group having as a substituent either an alkyl group or an aryl group, $R^{301}$ is an alkyl group or an aryl group, $R^{302}$, $R^{303}$ and $R^{304}$ are alkylene groups, h, j, k and 1 are integers of 0 or 1, and i is an integer of 2 to 200, and the plural i may be expressed in the same or different units).

$R^1$ and $R^2$ may together form a ring. This ring may have a heteroatom (e.g., an oxygen atom, a sulfur atom, a nitrogen atom) as an intra-ring atom.

In Formula (X), it is preferable that E is $NR^{101}$ and $R^{101}$ is a hydrogen atom or an alkyl group having 1 to 6 carbon atoms.

F is preferably an oxygen atom.

G is NH, i.e., $R^{202}$ is suitably a hydrogen atom.

It is also preferable that $R^{201}$ is an alkyl group having 1 to 6 carbon atoms, an alkoxy group having 1 to 6 carbon atoms, or an aryl group having 6 to 12 carbon atoms.

Particularly preferred groups represented by Formula (X) are as follows.

[CF 11]

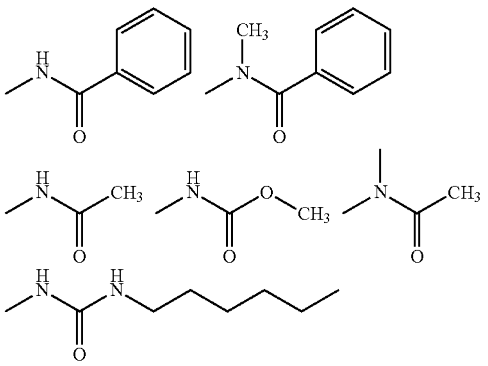

In Formula (Y), $R^{300}$ is preferably an alkylene group having 1 to 6 carbon atoms or a silylene group having as a substituent an alkyl group having 1 to 6 carbon atoms.

Preferably, $R^{30}1$ is an alkyl group having 1 to 6 carbon atoms.

$R^{302}$ is suitably an alkylene group having 1 to 6 carbon atoms.

$R^{303}$ is preferably an alkylene group having 1 to 6 carbon atoms.

$R^{304}$ is preferably an alkylene group having 1 to 6 carbon atoms.

Here, i is an integer of 2 to 200. Preferably, it is a number ranging from 5 to 100, more preferably from 8 to 75, and most preferably from 10 to 70.

Particularly suitable groups represented by Formula (Y) are represented by the following formula.

[CF 12]

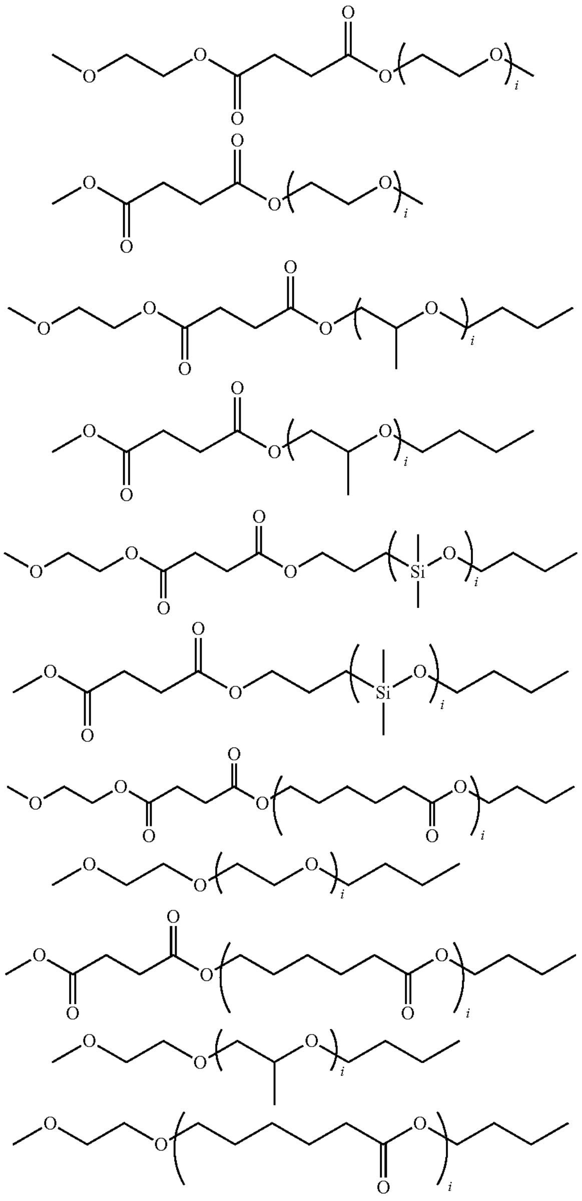

When a is 2, the two $R^1$ may be different from each other. In a case where a is 2 and the two $R^1$ are present adjacent to each other, the two $R^1$ may together form a ring, and the ring may have a heteroatom as an intra-ring atom.

In a case where b is 2 to 4, the plurality of $R^2$ may be different from each other. In a case where b is 2 to 4 and two $R^2$ are present adjacent to each other, the two adjacent $R^2$ may together form a ring that may have a heteroatom.

$R^3$ and $R^4$ are each a bonding hand to the divalent bridging group L or a group having the bonding hand, an aryl group or a heteroaryl group.

Further, in Formula (1), the divalent bridging group L is a group represented by Formula (3) below.

[CF 13]

$$-R^8-R^9-R^{10}- \quad (3)$$

As can be understood from Formula (3), the divalent bridging group L has a structure where $R^8$, $R^9$ and $R^{10}$ are linearly linked. Such a bridging group L includes an aromatic ring, and $R^8$ and $R^{10}$ are to be bonded to the PC. These structures will be described later in detail.

The photochromic cyclic compound of the present invention represented by Formula (1) has a cyclic structure having one or at least two photochromic basic structural groups PC. In particular, the bridging group L of Formula (3) is bonded to at least one ($R^3$ or $R^4$) at the 3-position of the naphthopyran structural group of Formula (2). The other of Formula (3) is bonded to $R^1$, $R^2$ of the naphthopyran structural group or the other of the 3-position (the other of $R^3$ or $R^4$) in a cyclic manner. In a particularly suitable example of bonds, the bridging group L is bonded to $R^3$ and $R^4$.

<Suitable Naphthopyran Structural Groups>

In the present invention, the naphthopyran structural group exhibited with PC is more preferably an indenonaphtopyran structural group having an indenonaphthopyran skeleton, and most preferably a structural group having an indeno[2,1-f]naphtho[1,2-b]pyran skeleton. In the present invention, at least one naphthopyran structural group forms a cyclic structure via a divalent bridging group, thereby exhibiting an excellent effect.

The structural group having an indeno[2,1-f]naphtho[1,2-b]pyran skeleton exemplified as the most preferred naphthopyran structural group is represented by Formula (4) below.

[CF 14]

(4)

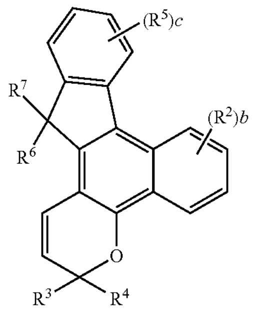

$R^2$, $R^3$, $R^4$ and b in Formula (4) are the same as those explained for Formula (2). In Formula (4), the structural moiety in which ($R^5$) c, $R^6$ and $R^7$ are present corresponds to the cyclic moiety formed with the two $R^1$ in Formula (2).

In Formula (4), $R^5$ is the same as the aforementioned $R^2$, which are specified below:

- a bonding hand to the divalent bridging group L or a group having the bonding hand;
- a hydroxyl group;
- an alkyl group (especially one having 1 to 6 carbon atoms); a cycloalkyl group (especially one having 3 to 8 carbon atoms);
- an alkoxy groups (especially one having 1 to 6 carbon atoms);
- an amino group;
- a heterocyclic group;
- a cyano group;
- a halogen atom;
- an alkylthio group;
- an arylthio group;
- a nitro group;
- a formyl group;
- a hydroxycarbonyl group;
- an alkylcarbonyl group (especially one having 2 to 7 carbon atoms);
- an alkoxycarbonyl group (especially one having 2 to 7 carbon atoms);
- an aralkyl group (especially one having 7 to 11 carbon atoms);
- an aralkoxy group (especially one having 7 to 11 carbon atoms);
- an aryloxy group (especially one having 6 to 12 carbon atoms);
- an aryl group (especially one having 6 to 12 carbon atoms); a heteroaryl group;
- a thiol group;
- an alkoxyalkylthio group (especially one having 3 to 8 carbon atoms);
- a cycloalkylthio group (especially one having 3 to 8 carbon atoms);
- Formula (X); and
- Formula (Y).

In Formula (4), c representing the number of $R^5$ is an integer of 0 to 4.

In a case where c is 2 to 4, the plurality of $R^5$ may be different from each other. In a case where c is 2 to 4 and two $R^5$ are present adjacent to each other, the two $R^5$ may together form a ring. This ring may contain a hetero atom (an oxygen atom, a sulfur atom, a nitrogen atom, or the like).

$R^6$ and $R^7$ are each as follows:

- a bonding hand to the divalent bridging group L;
- a hydrogen atom;
- a hydroxyl group;
- an alkyl group (especially one having 1 to 6 carbon atoms);
- a cycloalkyl group (especially one having 3 to 8 carbon atoms);
- an alkoxy group (especially one having 1 to 6 carbon atoms);
- an alkoxyalkyl group;
- a formyl group;
- a hydroxycarbonyl group;
- an alkylcarbonyl group (especially one having 2 to 7 carbon atoms);
- an alkoxycarbonyl group (especially one having 2 to 7 carbon atoms);
- a halogen atom;
- an aralkyl group (especially one having 7 to 11 carbon atoms);
- an aralkoxy group (especially one having 7 to 11 carbon atoms);
- an aryloxy group (especially one having 6 to 12 carbon atoms);
- an aryl group (especially one having 1 to 6 carbon atoms); a heterocyclic group;
- Formula (X); and
- Formula (Y).

Further, the $R^6$ and $R^7$ together may form an aliphatic ring having 3 to 20 membered carbon atoms, a fused polycyclic ring having an aromatic ring or an aromatic heterocyclic ring fused with the aliphatic ring, a heterocyclic ring having 3 to 20 membered atoms, or a fused polycyclic ring having an aromatic ring or an aromatic heterocyclic ring fused with the heterocyclic ring.

In the indenonaphthopyran structural group of Formula (4), the following embodiments are particularly suitable.

$R^2$ is preferably an alkyl group having 1 to 6 carbon atoms, an alkoxy group having 1 to 6 carbon atoms, a substituted amino group, a heterocyclic group, an alkylthio group, an arylthio group, or an aryl group having 6 to 12 carbon atoms.

Further preferably, these $R^2$ are present at 6-position and/or 7-position of the indeno[2, 1-f]naphtho[1, 2-b]pyran. It is also suitable that the $R^2$ are present at the 6- and 7-positions, thereby forming together an aliphatic ring. The aliphatic ring may contain an oxygen atom, a nitrogen atom, or a sulfur atom, as an intra-ring atom. Needless to note, the ring may further have a substituent. In addition, further preferably the intra-ring atom of the aliphatic ring (including a hetero atom) is 5 to 8. The substituent possessed by the aliphatic ring is preferably an alkyl group having 1 to 6 carbon atoms.

$R^5$ is preferably a hydrogen atom (when b=0), an alkyl group having 1 to 6 carbon atoms, an alkoxy group having 1 to 6 carbon atoms, an aryl group having 6 to 12 carbon atoms, or an arylthio group. It is more preferred that these groups be present at the 11-position of indeno[2,1-f]naphtho[1,2-b]pyran.

It is further suitable that both $R^3$ and $R^4$ be bonded to the divalent bridging group L. That is, it is preferable that $R^3$ is bonded to one side of the bridging group L while $R^4$ is bonded to the other side of the bridging group L, thereby forming a ring. By forming a ring of this structure, the molecular motion of the ring opening and the ring closing is moderately controlled, whereby the temperature dependence of the photochromic cyclic compound can be reduced.

Further, when improvement of the temperature dependence is taken into consideration, $R^6$ and $R^7$ are each preferably an alkyl group having 1 to 12 carbon atoms.

In another suitable embodiment, $R^6$ and $R^7$ together form a ring. The ring contains a 13-position carbon atom to which $R^6$ and $R^7$ bond, and the example may include the following rings, as mentioned above:

- an aliphatic ring having 3 to 20 membered carbon atoms;
- a fused polycyclic ring in which an aromatic ring or an aromatic heterocyclic ring is fused with the aliphatic ring;
- a heterocyclic ring having 3 to 20 membered carbon atoms; and
- a fused polycyclic ring in which an aromatic ring or an aromatic heterocyclic ring is fused with the heterocyclic ring.

In a case where a ring as described above is formed with $R^6$ and $R^7$, it is more preferable that an aliphatic ring that makes a spiro structure with the carbon at 13-position located in the 5-membered ring of indenonaphthopyran is formed. Suitable examples of the ring to form the spiro structure include:

- a cyclopetane ring;
- a cyclohexane ring;
- a cycloheptane ring;
- a cyclooctane ring;
- a cyclononane ring;
- a cyclodecane ring;
- a cycloundecane ring;
- a cyclododecane ring; and
- a spirodicyclohexane ring.

It is also suitable that a substituent is introduced into the ring formed by combining $R^6$ and $R^7$, in particular, a ring to form a spiro structure. For instance, 1 to 10 substituents may be introduced, and the substituent is an alkyl group having 1 to 3 carbon atoms or a cycloalkyl group having 5 to 7 carbon atoms. Alternatively, a cycloalkyl group having 5 to 7 carbon atoms may be fused therewith.

Examples of particularly suitable ring as a ring formed with $R^6$ and $R^7$ are as follows.

[CF 15]

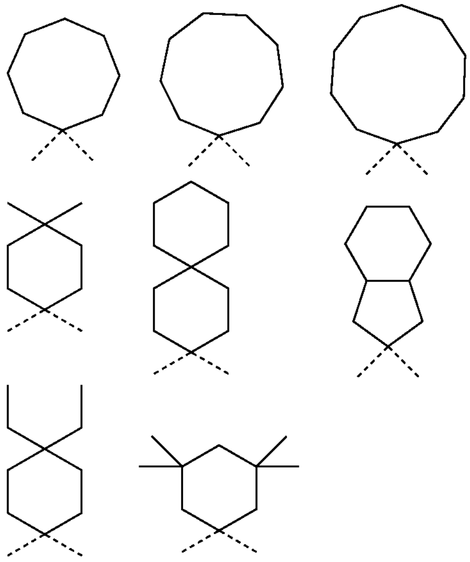

<Divalent Bridging Group L>

In Formula (1), the divalent bridging group represented by L has a structure in which $R^8$, $R^9$ and $R^{10}$ are linearly linked as represented by Formula (3) below, as briefed above.

[CF 16]

$$-R^8-R^9-R^1 \quad (3)$$

$R^8$, $R^9$ and $R^{10}$ indicate the following groups (or direct bonding hands), provided that not all of them become the direct bonding hands at the same time.

$R^8$ and $R^{10}$ are direct bonding hands, or aromatic ring groups having 6 to 30 carbon atoms. The groups are rigid and prone to intermolecular interactions such as r-r stacking.

Representatives of the aromatic ring groups include a benzene-based aromatic ring group and a heteroaromatic ring group, and the benzene-based aromatic ring group is particularly suitable. As the benzene-based aromatic ring to form this ring group, a benzene ring and a fused polycyclic aromatic ring obtained by fusing a plurality of benzene rings are preferred, and the benzene ring is particularly suitable.

Accordingly, a particularly suitable group for $R^8$ and $R^{10}$ is a p-phenylene group.

$R^9$ located between $R^8$ and $R^{10}$ may be a direct bonding hand or a divalent organic group.

Examples of the organic group include: a saturated or unsaturated polyvalent hydrocarbon group having 1 to 15 carbon atoms; a saturated or unsaturated polyvalent (hetero) cycloalkylene group having 3 to 20 carbon atoms; an oxygen atom; a sulfur atom; a polyvalent amino group; a polyvalent silylene group having 1 to 3 silicon atoms, which has, as a substituent, at least one group selected from an alkyl group having 1 to 15 carbon atoms, an alkoxy group having 1 to 15 carbon atoms, or an aromatic ring group having 6 to 30 carbon atoms; and a group composed of a combination of these groups.

Preferred examples of $R^9$ include: a direct bonding hand, a methylene group, an ethylene group, an ethylene oxy group, a vinylene group, an ethynylene group, a cyclohexylene group, a phenylene group, an oxygen atom, a sulfur atom, a polyvalent amino group, an azo group, a dimethylsilylene group, a dimethylsiloxy group, or a combination thereof. Particularly preferred examples include: a direct bonding, a methylene group, a phenylene group, a cyclohexylene group, an oxygen atom, a sulfur atom, a polyvalent amino group, an ethyleneoxy group, a dimethylsilylene group, a dimethylsiloxy groups, or a combination thereof.

$R^8$ is a phenylene group, which is the smallest one in aromatic group, and $R^9$ and $R^{10}$ make a direct bond, the lower limit will be 72.

Examples of particularly suitable bonding hands are shown below. Here, m is 1 to 30.

[CF 17]

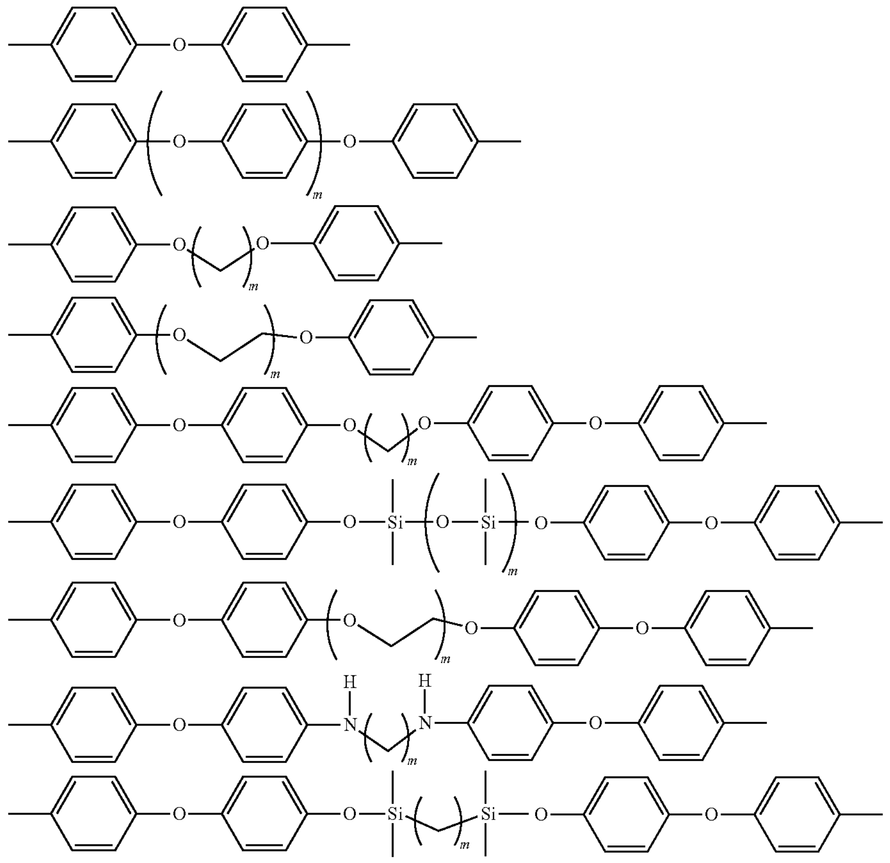

Examples of combination group are as follows. A group composed of one oxygen atom and one phenylene group (Ph) is a group —O-Ph-. And a group composed of two oxygen atoms and one phenylene group is a group —O-Ph-O—.

In the present invention, in view of improvement in the temperature dependence, preferably at least either $R^8$ or $R^{10}$ is an aromatic ring group having 6 to 30 carbon atoms, since it is rigid and likely to undergo intermolecular interactions such as π-π stacking.

In view of the effects of the present invention, it seems to be preferable that the molecular weight of L composed of $R^8$ to $R^{10}$ is not excessively increased. In other words, if L to be linked to the PC becomes too long (that is, the molecular weight becomes too large), the effect of the present invention may be difficult to be exhibited. For this reason, the molecular weight of L is preferably less than 1500, more preferably less than 1250, still more preferably less than 1000, and particularly preferably less than 850, although there is no particular limitation thereof.

The lower limit of L is not particularly limited, and it relies on the combination of $R^8$, $R^9$ and $R^{10}$. For instance, if <n>

In Formula (1), n is a number of 1 or larger, and it indicates the number of repeating units [-PC-L-] of PC (naphthopyran structural group) and the bridging group L. If this n becomes too large, the effect tends to decrease, and production of the photochromic cyclic compound tends to be difficult. In light of this, the upper limit of n is preferably 20 or less, more preferably 10 or less, and particularly preferably 8 or less.

When n is 2 or more, there is no particular limitation for the plurality of PC. All of the PC may be identical or PCs having different structures may be mixed. However, all of the PC are preferably of the same kind from the viewpoint of production.

<Specific Examples of Photochromic Cyclic Compound>

For the photochromic cyclic compound of the present invention, the aforementioned combination of PC, L, and n may be appropriately selected, and will not be limited to the examples of compounds indicated with the formulae below.

Examples of Photochromic Cyclic Compounds in a Case where n is 1

[CF 18]
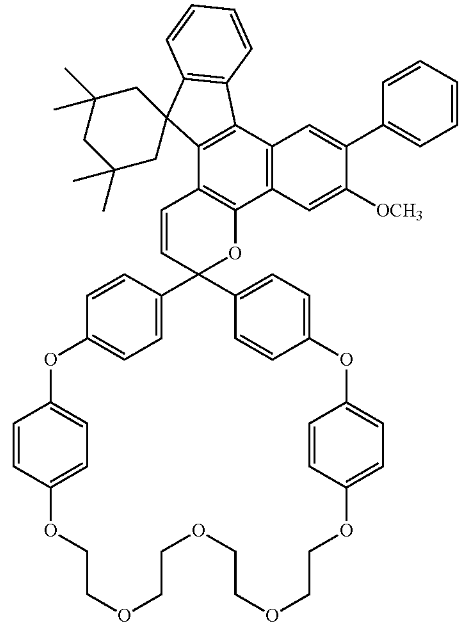
-continued
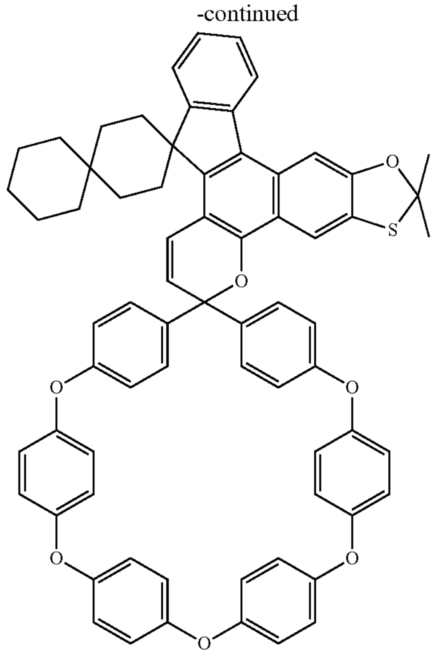
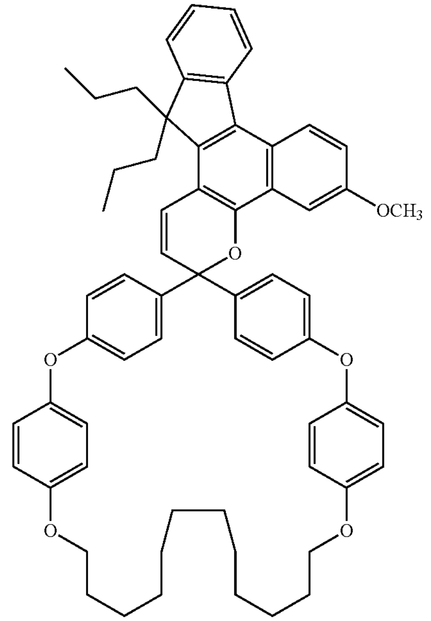
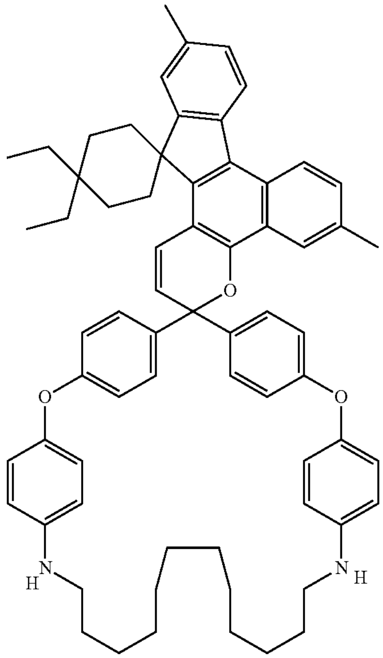

-continued
[CF 19]
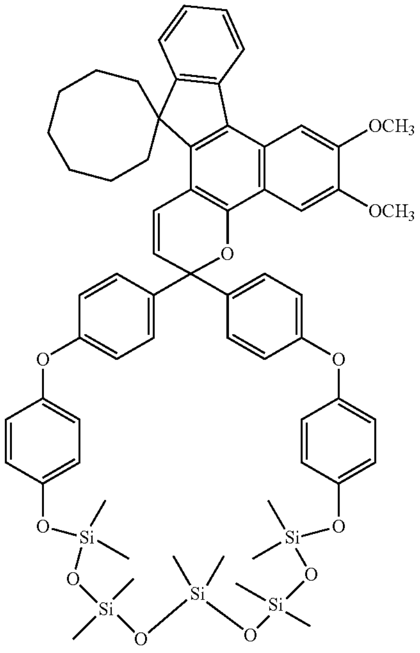
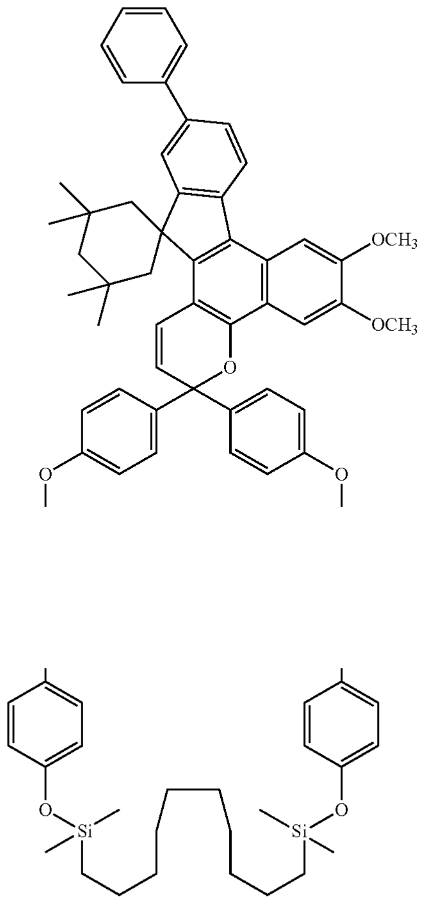
-continued
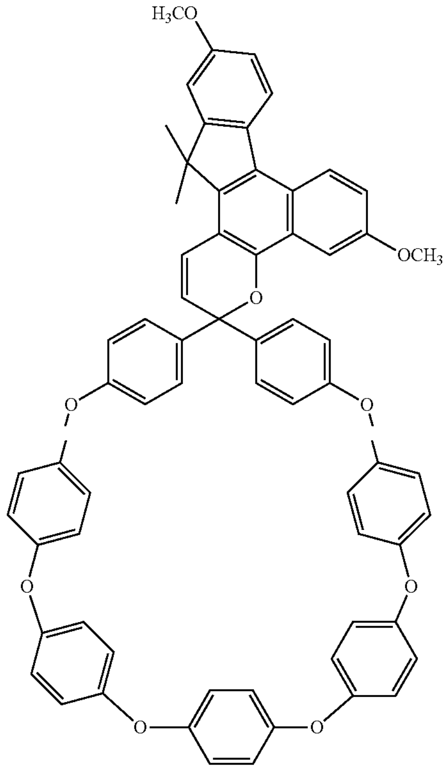
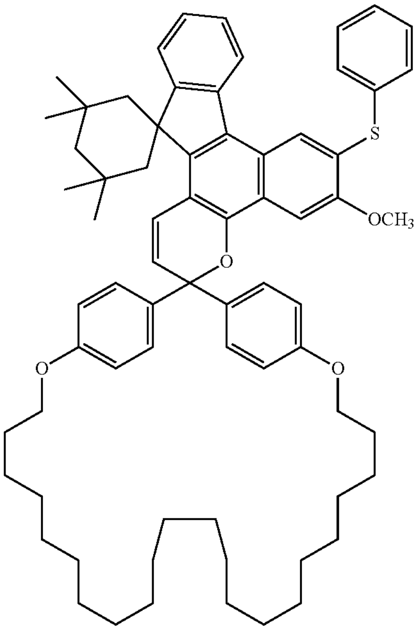

Examples of Photochromic Cyclic Compound in a Case where n is 2 or Larger
[CF 20]
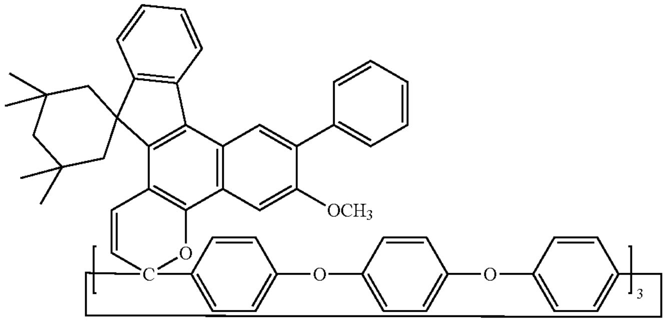
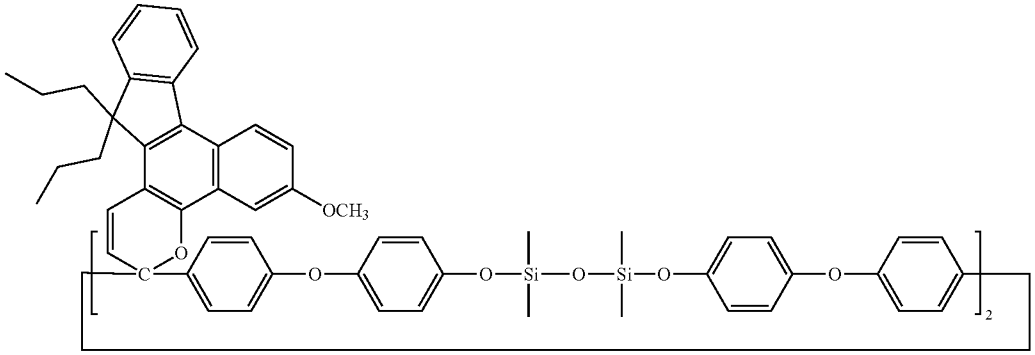
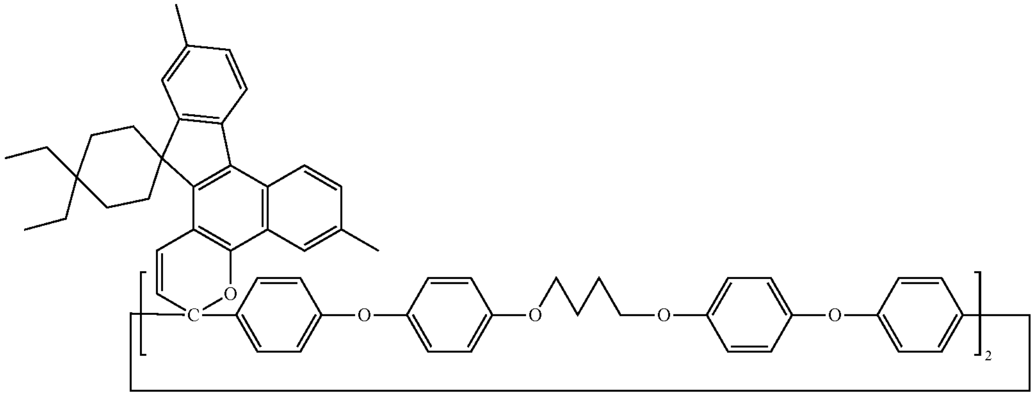
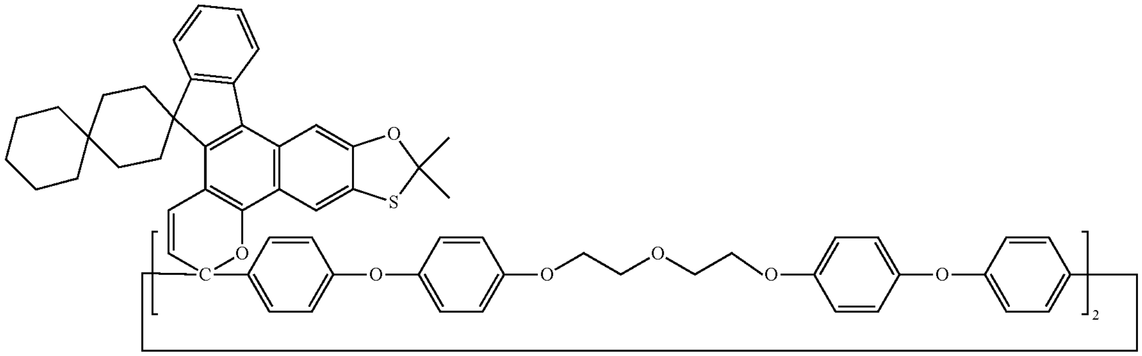

-continued
[CF21]
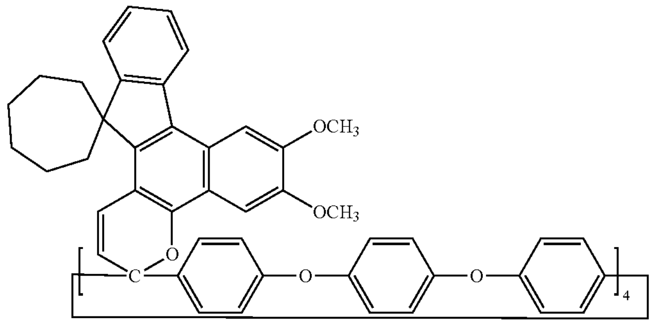
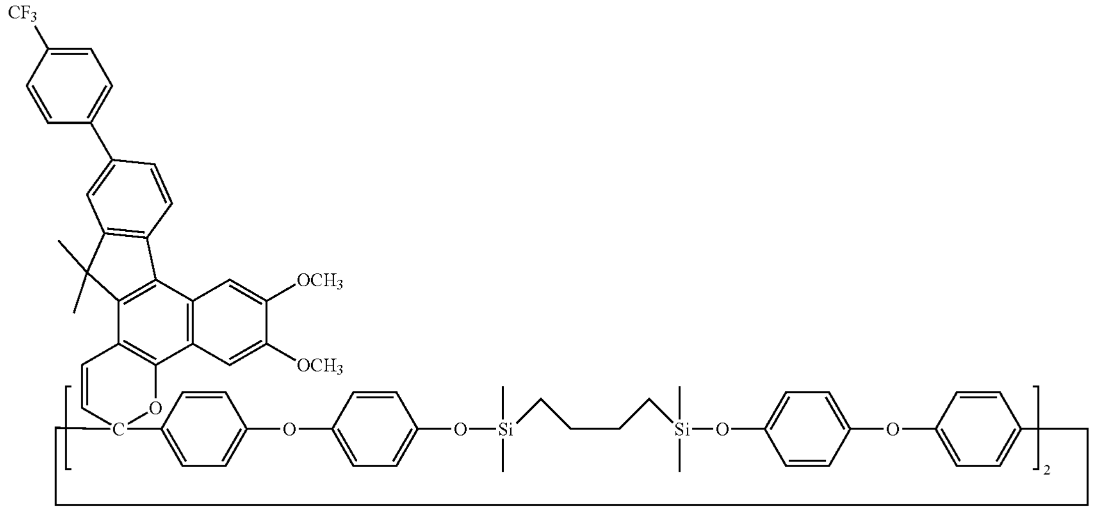
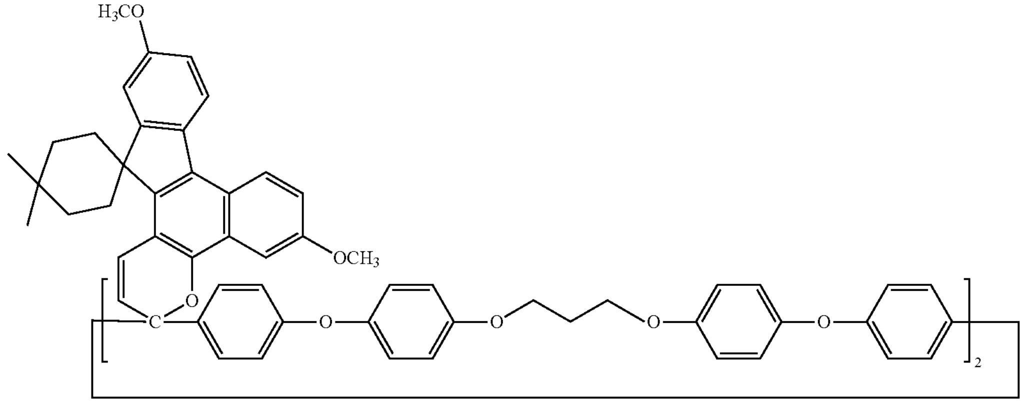
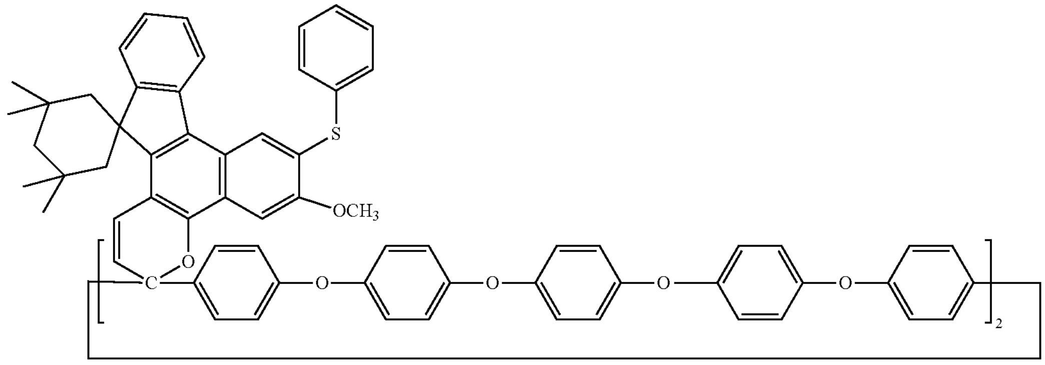

<Identification of Photochromic Cyclic Compound>

The photochromic cyclic compound of the present invention, which is usually present as a solid at ordinary temperature and pressure, can be confirmed in the following manner: (1) or (2).

(A) The following peaks are measured in the proton nuclear magnetic resonance ($^1$H-NMR) spectrum.

δ: around 5.0 to 9.0 ppm (a peak due to aromatic protons and alkene protons)

δ: around 1.0 to 4.0 ppm (a peak due to protons of alkyl groups and alkylene groups)

The number of protons in the respective bonding groups can be determined by a relative comparison of the spectral intensities. This allows for the identification of the divalent bridging group L.

(B) The following peaks are measured in the $^{13}$C-nuclear magnetic resonance ($^{13}$C-NMR) spectrum.

δ: around 110 to 160 ppm (a peak due to carbons of aromatic ring groups)

δ: around 80 to 140 ppm (a peak due to carbons of alkenes and alkynes)

δ: around 20 to 80 ppm (a peak due to carbons of alkyl groups and alkylene groups)

<Production of Photochromic Cyclic Compound>

The photochromic cyclic compound of the present invention can be synthesized by any of various methods.

For instance, a photochromic cyclic compound of Formula (5) below having an indenonaphthopyran structural group can be suitably produced by the method described below. In the following description, references in each formula are the same as those in the above-described formulas unless otherwise specified.

[CF 22]

(5)

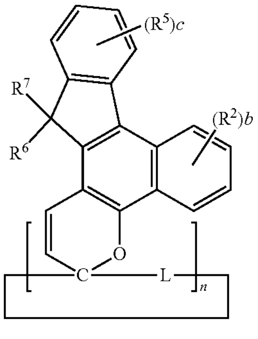

More specifically, it is possible to suitably produce the photochromic cyclic compound by reacting a naphthol compound represented by Formula (6) below with a cyclic propargyl alcohol compound represented by Formula (7) below in a solvent in the presence of an acid catalyst.

[CF 23]

(6)

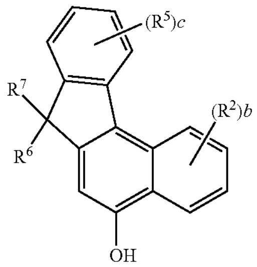

[CF 24]

(7)

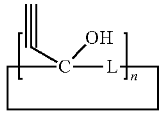

As the acid catalyst, sulfuric acid, benzenesulfonic acid, p-toluenesulfonic acid, acidic alumina or the like is used, for instance.

The acid catalyst is preferably used in the range of 0.1 to 10 parts by mass relative to totally 100 parts by mass of the naphthol compound and the cyclic propargyl alcohol compound. The reaction temperature is preferably 0 to 200° C.

As the solvent, preferably an aprotic organic solvent is used, and the examples include N-methylpyrrolidone, dimethylformamide, tetrahydrofuran, benzene, toluene, methyl ethyl ketone, and methyl isobutyl ketone.

There is no particular limitation on the method for purifying the product obtained by the reaction. It is possible to purify the product, for instance, by silica gel column purification and further recrystallization.

As the naphthol compound represented by Formula (6), any appropriate compound can be used in accordance with the structure of the target photochromic cyclic compound. Example thereof are as follows.

[CF25]

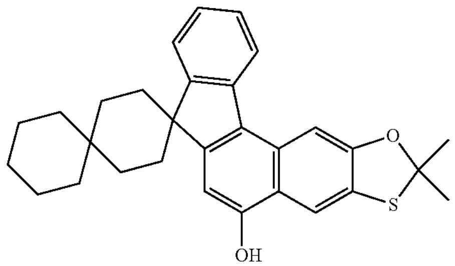

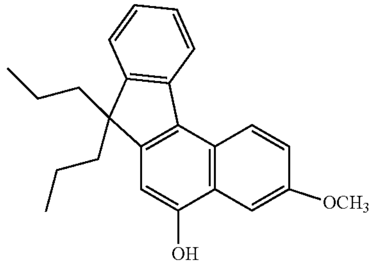

-continued

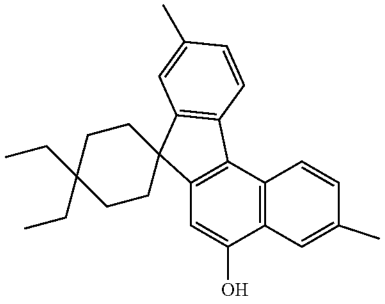

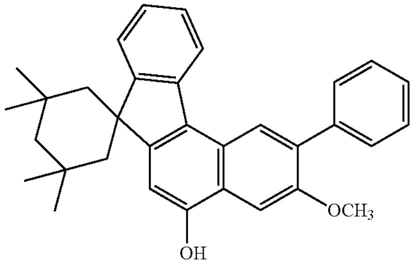

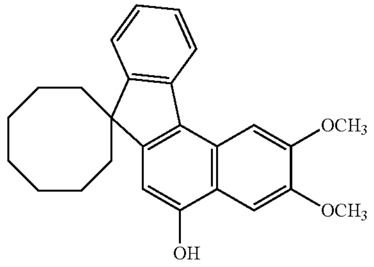

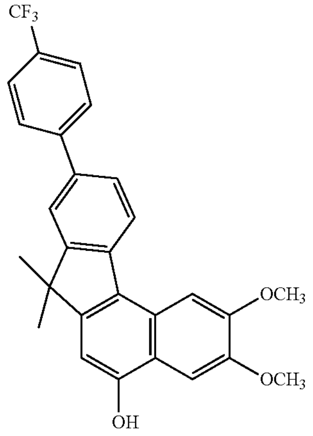

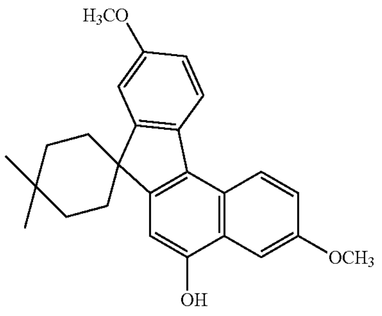

-continued

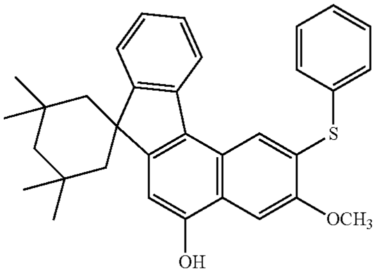

[CF26]

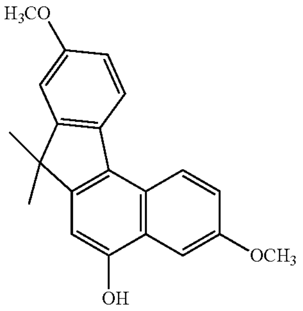

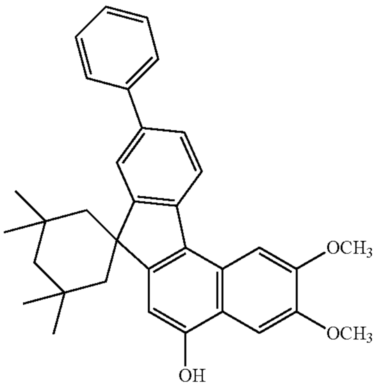

The naphthol compound of Formula (6) can be synthesized for instance, by the methods described in pamphlets of WO 2001/60881, WO 2005/028465 and the like.

Specifically, a benzophenone compound represented by Formula (8) below is prepared first.

[CF 27]

(8)

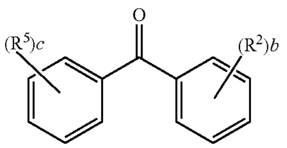

The benzophenone compound is used for performing the Stobbe reaction, a cyclization reaction, a hydrolysis reaction using an alkali or an acid, benzyl protection, and further debenzylation by the hydrolysis reaction using an alkali or an acid, thereby obtaining a benzyl protected carboxylic acid represented by Formula (9) below. These reactions are known per se. In Formula (9), Bn is a benzyl group.

[CF 28]

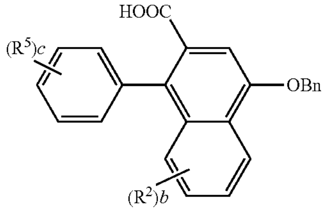
(9)

The carboxylic acid is converted into an amine by the Curtius rearrangement, the Hofmann rearrangement, the Lossen rearrangement or the like, from which a diazonium salt is prepared by a method known per se.

The diazonium salt is converted into a bromide by the Sandmeyer reaction or the like, and the thus-obtained bromide is reacted with magnesium, lithium or the like to prepare an organometallic compound. The organometallic compound is reacted with a ketone represented by Formula (10) below in an organic solvent at −80° C. to 70° C. for 10 minutes to four hours, thereby obtaining an alcohol compound.

[CF 29]

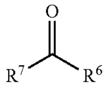
(10)

The thus-obtained alcohol compound is subjected to the Friedel-Crafts reaction. More specifically, the alcohol compound is reacted under neutral to acidic conditions at 10° C. to 120° C. for 10 minutes to two hours, so that the alcohol moiety is converted by a nucleophilic substitution reaction, thereby synthesizing the naphthol compound represented by Formula (6).

[CF 30]

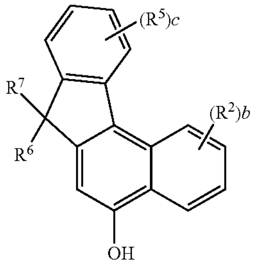
(6)

In this reaction, the reaction ratio of the organometallic compound to the ketone represented by Formula (10) is preferably selected from a range of 1:10 to 10:1 (molar ratio). The reaction temperature is preferably −80° C. to 70° C. The suitable solvent is an aprotic organic solvent such as diethyl ether, tetrahydrofuran, benzene, or toluene.

The Friedel-Crafts reaction is preferably performed using an acid catalyst such as acetic acid, hydrochloric acid, sulfuric acid, benzenesulfonic acid, p-toluenesulfonic acid, or acidic alumina. This reaction uses an aprotic organic solvent such as tetrahydrofuran, benzene, or toluene.

The cyclic propargyl alcohol compound represented by Formula (7) can be easily synthesized by reacting a cyclic ketone compound corresponding to the compound with a metal acetylene compound such as lithium acetylide.

The photochromic cyclic compound of the present invention, which is synthesized as described above, is well soluble in a common organic solvent such as toluene, chloroform, or tetrahydrofuran. When the photochromic cyclic compound of the present invention is dissolved in such a solvent, the resultant solution, which is usually almost colorless and transparent, exhibits a good photochromic action such that it rapidly gets into a color developed state when irradiated with sunlight or ultraviolet rays, while it rapidly returns to its original colorless state reversibly when the light is blocked.

It is also possible to use a combination of plural kinds of photochromic cyclic compounds of the present invention in accordance with the desired color tones in order to obtain various color tones required for a photochromic lens.

The photochromic cyclic compound of the present invention can be used as a photochromic composition in combination with another photochromic compound depending on the intended use as long as the effects of the present invention are not impaired. Example of the other photochromic compound to be combined are any known compound (for instance, fulgide, flugimide, spirooxazine, or chromene), which can be used without any substantial limitation.

Among them, a chromene compound is particularly preferred because uniform color tones can be kept at the time of color development and fading; color distortion at the time of color development due to a deterioration in photochromic properties can be prevented; and initial coloration can be reduced. When the photochromic cyclic compound of the present invention is used in combination with another photochromic compound, the blending ratio of each of the compounds is appropriately determined depending on the desired color tone.

The photochromic cyclic compound of the present invention can be widely used as a photochromic material. The examples include optical materials, various memory materials as a replacement for a silver halide photosensitive material, such as a copying material, a printing photoreceptor, a memory material for cathode-ray tubes, a photosensitive material for lasers, and a photosensitive material for holography. In addition, a photochromic material using the photochromic cyclic compound of the present invention can also be used as a photochromic lens material, an optical filter material, a display material, an actinometer material, a decoration material and the like.

<Photochromic Curable Composition>

The photochromic cyclic compound of the present invention can be used as a photochromic curable composition in combination with a polymerizable compound.

Preferable blending ratios of the compositions of the photochromic curable composition are as follows, though the ratios may vary depending on the color development intensity of the photochromic cyclic compound, the selected lens material, and the thickness of the lens.

For instance, it is suitable to use the photochromic cyclic compound of the present invention in an amount of 0.001 to 10 parts by mass relative to 100 parts by mass of the polymerizable compound.

The optimum blending amount can be adjusted depending on the use. The following examples refer to a case of using the photochromic curable composition as a thin-film optical article and a case of using the photochromic curable composition as a thick-film optical article.

In a case where the photochromic curable composition is a thin film like a coating, for instance, a thin film of about 100 μm (a polymer film obtained by polymerizing the photochromic curable composition), it is preferable to adjust the color tone with 0.001 to 10 parts by mass of the photochromic cyclic compound of the present invention relative to 100 parts by mass of the polymerizable compound.

In a case where the photochromic curable composition is a thick cured body (a polymer molded body formed by polymerizing the photochromic curable composition), for instance, in a case where the composition is a cured body having a thickness of 1 mm or more, it is preferable to adjust the color tone with 0.001 to 1 part by mass of the photochromic cyclic compound of the present invention relative to 100 parts by mass of the thick cured body or the polymerizable compound imparting a thick cured body.

<Polymerizable Compound>

As described above, it is possible to combine the photochromic cyclic compound of the present invention and a polymerizable compound so as to be used as a photochromic curable composition.

Examples of the polymerizable compound include a urethane- or urea-based polymerizable compound capable of forming a urethane bond, a urea bond, and the like, a radically polymerizable compound, and an epoxy-based polymerizable compound. Although these polymerizable compounds are not particularly limited, the polymerizable compound described in WO 2018/235771 can be suitably used, for instance. Among them, a urethane-based polymerizable compound or a radically polymerizable compound described below is suitably used.

(Urethane-Based Polymerizable Compound)

As the urethane-based polymerizable compound, a composition containing an iso(thio)cyanate compound and a compound having an active hydrogen can be suitably used.

Iso(Thio)Cyanate Compound

An iso(thio)cyanate compound is a compound having an isocyanate group or an isothiocyanate group, and it may contain both the isocyanate group and the isothiocyanate group. This compound is suitably used in combination with any of the following compounds containing active hydrogen.

Examples of the iso (thio) cyanate compounds are as follows, though the compounds are not limited to these examples:

- polyiso(thio)cyanate having at least two iso(thio)cyanate groups in one molecule;
- aromatic polyiso(thio)cyanate having an aromatic ring such as m-xylene diisocyanate or 4,4'-diphenylmethane diisocyanate; and
- aliphatic polyiso(thio)cyanate such as norbornane diisocyanate or dicyclohexylmethane-4,4'-diisocyanate.

Compound Having Active Hydrogen

The compound having active hydrogen is preferably a compound having a hydroxyl group and/or a thiol group, and particularly preferably, a polyfunctional compound having two or more active hydrogens in one molecule, though the present invention is not limited thereto. Specific examples of the compound having active hydrogen include polyfunctional thiol compounds such as pentaerythritoltetrakis(3-mercaptopropionate) and 4-mercaptomethyl-3,6-dithia-octanedithiol, and polyfunctional alcohols such as trimethylolpropane and pentaerythritol.

(Radically Polymerizable Compound)

The radically polymerizable compound can be classified into a polyfunctional radically polymerizable compound and a monofunctional radically polymerizable compound, each of which can be used alone, or a plurality of the compounds can be used in combination. Examples of the radically polymerizable substituent include a group having an unsaturated double bond, that is, a vinyl group (including a styryl group, a (meth)acrylic group, an allyl group, and the like).

The polyfunctional radically polymerizable compound is a compound having two or more radically polymerizable substituents in a molecule. This polyfunctional radically polymerizable compound can be classified into a first polyfunctional radically polymerizable compound having 2 to 10 radically polymerizable substituents and a second polyfunctional radically polymerizable compound having more than 10 radically polymerizable substituents.

The first radically polymerizable compound is not particularly limited, but preferably it has 2 to 6 radically polymerizable substituents. Specific examples thereof are as follows:

- polyfunctional (meth)acrylic ester compounds:
  - ethylene glycol di(meth)acrylate,
  - diethylene glycol di(meth)acrylate,
  - triethylene glycol di(meth)acrylate,
  - tetraethylene glycol di(meth)acrylate,
  - ethylene glycol bisglycidyl(meth)acrylate,
  - bisphenol A di(meth)acrylate,
  - 2,2-bis(4-(meth)acryloyloxyethoxyphenyl)propane, and
  - 2,2-bis(3,5-dibromo-4-(meth)acryloyloxyethoxyphenyl) propane;
- polyfunctional allylic compounds:
  - diallyl phthalate,
  - diallyl terephthalate,
  - diallyl isophthalate,
  - diallyl tartrate,
  - diallyl epoxy succinate,
  - diallyl fumarate,
  - diallyl chlorendate,
  - diallyl hexaphthalate,
  - diallyl carbonate,
  - allyl diglycol carbonate, and
  - trimethylolpropane triallyl carbonate;
- polyfunctional thio(meth)acrylic ester compounds:
  - 1,2-bis(methacryloylthio)ethane,
  - bis(2-acryloylthioethyl)ether, and
  - 1,4-bis(methacryloylthiomethyl)benzene; and vinyl compounds:
  - divinylbenzene.

Examples of the second polyfunctional radically polymerizable compound having more than 10 radically polymerizable substituents include compounds having a relatively large molecular weight, such as a silsesquioxane compound having radically polymerizable substituents and a polyrotaxane compound having radically polymerizable substituents.

The monofunctional radically polymerizable compound is a compound having one radically polymerizable substituent in a molecule, and specific examples thereof include the following compounds, though the present invention is not limited thereto.

Unsaturated Carboxylic Acids:

- acrylic acid,
- methacrylic acid, and
- maleic anhydride;
- (meth)acrylic acid esters:
  - methyl(meth)acrylate, benzyl methacrylate,
phenyl methacrylate,
2-hydroxyethyl methacrylate,
glycidyl (meth)acrylate,
β-methylglycidyl (meth)acrylate,
bisphenol A-monoglycidyl ether-methacrylate,
4-glycidyloxymethacrylate,
3-(glycidyl-2-oxyethoxy)-2-hydroxypropyl methacrylate,
3-(glycidyloxy-1-isopropyloxy)-2-hydroxypropylacrylate, and
3-(glycidyloxy-2-hydroxypropyloxy)-2-hydroxypropylacrylate;

fumaric acid esters:
diethyl fumarate, and
diphenyl fumarate;

thio(meth)acrylic acids:
methylthioacrylate,
benzylthioacrylate, and
benzylthiomethacrylate; and vinyl compounds:
styrene,
chlorostyrene,
methylstyrene,
vinylnaphthalene,
α-methylstyrene dimer, and
bromostyrene.

The radically polymerizable compound may be used alone, or a mixture of a plurality thereof may be used. In this case, the amount of the polyfunctional radically polymerizable compound is preferably set to 80 to 100 parts by mass, and the amount of the monofunctional radically polymerizable compound is preferably set to 0 to 20 parts by mass, relative to 100 parts by mass of the total of the radically polymerizable compounds. More preferably, the polyfunctional radically polymerizable compound is set to 90 to 100 parts by mass, and the monofunctional radically polymerizable compound is set to 0 to 10 parts by mass. Further, it is preferable to set the first polyfunctional radically polymerizable compound to 80 to 100 parts by mass, the second radically polymerizable compound to 0 to 20 parts by mass, and the monofunctional radically polymerizable compound to 0 to 20 parts by mass, relative to 100 parts by mass of the total of the radically polymerizable compounds. And it is further preferable to set the first polyfunctional radically polymerizable compound to 85 to 100 parts by mass, the second polyfunctional radically polymerizable compound to 0 to 10 parts by mass, and the monofunctional radically polymerizable compound to 0 to 10 parts by mass.

Compounding Agents

Various compounding agents known per se may be blended in the curable composition of the present invention, within a range not impairing the effect of the present invention, and the examples include a mold release agent, an ultraviolet absorber, an infrared absorber, an ultraviolet stabilizer, an antioxidant, a coloring inhibitor, an antistatic agent, a fluorescent dye, a dye, a pigment, and a perfume. A solvent or a leveling agent also may be blended. Furthermore, thiols such as t-dodecylmercaptan may be blended as a polymerization modifier, if necessary.

Among these agents, the ultraviolet stabilizer is suitable from the viewpoint that the durability of the photochromic moiety can be improved. As the ultraviolet stabilizer, a hindered amine light stabilizer, a hindered phenol antioxidant, a sulfur-based antioxidant and the like are known. Particularly suitable ultraviolet stabilizers are as follows:

bis(1,2,2,6,6-pentamethyl-4-piperidyl) sebacate;
ADK STAB® LA-52, LA-57, LA-62, LA-63, LA-67, LA-77, LA-82, and LA-87 manufactured by ADEKA CORPORATION;
2,6-di-tert-butyl-4-methyl-phenol;
ethylenebis(oxyethylene)bis[3-(5-tert-butyl-4-hydroxy-m-tolyl)propionate]; and
IRGANOX® 1010, 1035, 1075, 1098, 1135, 1141, 1222, 1330, 1425, 1520, 259, 3114, 3790, 5057, and 565 manufactured by Ciba Specialty Chemicals.

Though the use amount of the ultraviolet stabilizer is not particularly limited as long as the effect of the present invention is not impaired, usually it is in the range of 0.001 to 10 parts by mass, particularly 0.01 to 1 part by mass, relative to 100 parts by mass of the photochromic hydroxyurethane compound of the present invention. In particular, in a case of using a hindered amine light stabilizer, the effect of improving durability may vary depending on the type of photochromic moiety, and as a result, a color deviation may occur in the adjusted color tone at the time of color development. In order to prevent or reduce the color distortion, the blending amount is preferably set to 0.5 to 30 mol, more preferably 1 to 20 mol, and still more preferably 2 to 15 mol, per mol of the photochromic moiety.

Besides the ultraviolet stabilizer, an ultraviolet absorber can also be used. Known ultraviolet absorbers are available, such as a benzophenone-based compound, a benzotriazole-based compound, a cyanoacrylate-based compound, a triazine-based compound, and a benzoate-based compound. In particular, a cyanoacrylate-based compound and a benzophenone-based compound are preferred. The ultraviolet stabilizer is preferably used in an amount in a range of 0.001 to 5 parts by mass relative to 100 parts by mass of the photochromic curable composition containing the photochromic compound and the polymerizable compound.

<Method of Using Photochromic Curable Composition; Optical Article>

A polymerized photochromic curable composition of the present invention can be used as a photochromic optical article. The photochromic curable composition can be prepared by mixing a photochromic cyclic compound and a polymerizable compound to be used, an additive and the like to be blended if necessary, by a known method.

Polymerization for producing a photochromic optical article is performed by radical polymerization, ring-opening polymerization, anionic polymerization or condensation polymerization by irradiation with active energy rays such as ultraviolet rays, α rays, β rays or γ rays, by heating or a combination thereof, for instance. In other words, any appropriate polymerization means may be employed in accordance with the type of the polymerizable compound and the polymerization curing accelerator and the form of the photochromic optical article to be formed.

At the time of thermally polymerizing the photochromic curable composition of the present invention, the temperature affects the properties of the photochromic optical article to be obtained. The temperature condition cannot be definitely limited as it is under the influence of the type and amount of the thermal polymerization initiator and the type of the polymerizable compound. Usually, however, a method in which polymerization is started at a relatively low temperature, which is then slowly raised, is suitable. As for the polymerization time, which also varies with various factors just like the temperature, it is suitable to determine in advance the optimal time depending on the conditions. It is usually preferable to select the condition so that polymerization is completed in 2 to 48 hours.

In the photopolymerization of the photochromic curable composition of the present invention, the UV intensity as one of the polymerization conditions particularly affects the properties of the photochromic optical article to be obtained. The illumination condition cannot be definitely limited because it is under the influence of the type and amount of the photopolymerization initiator and the type of the polymerizable monomer. However, it is usually preferable to select the condition so that UV light of 50 to 500 $mW/cm^2$ is irradiated at a wavelength of 365 nm for 0.5 to 5 minutes.

For instance, as for a photochromic lens, any known method described below can be employed as long as uniform dimming performance is achieved.

In a case of producing a photochromic lens by a kneading method, the aforementioned photochromic curable composition is injected between glass molds held by an elastomer gasket or a spacer, followed by cast polymerization with heat in an air furnace or by irradiation with active energy rays such as ultraviolet rays depending on the type of the polymerizable compound and the polymerization curing accelerator, thereby obtaining a photochromic optical article molded into a form of a lens or the like.

In a case of producing a photochromic lens by a lamination method, the photochromic curable composition is appropriately dissolved in an organic solvent to prepare a coating liquid, and the coating liquid is applied to a surface of an optical base material such as a lens base material by spin coating, dipping, or the like, dried to remove the organic solvent, and then, UV-irradiated or heated in an inert gas such as nitrogen or the like to perform polymerization. In this manner, a photochromic optical article having a photochromic layer formed on the surface of the optical base material can be obtained (coating method).

Alternatively, an optical base material like a lens base material is disposed facing the glass mold so as to form a predetermined void, into which the photochromic curable composition is injected, and polymerization is performed by UV irradiation, heating or the like, that is, a cast polymerization by innermold, whereby a photochromic optical article having a photochromic layer formed on an optical base material can be obtained (cast polymerization method).

In a case of forming a photochromic layer on the surface of the optical base material by the lamination method (coating method and cast polymerization method) as described above, it is also possible to subject in advance the surface of the optical base material to a chemical treatment with an alkaline solution, an acid solution or the like, or a physical treatment by corona discharge, plasma discharge, polishing or the like so as to enhance the adhesion between the photochromic layer and the optical base material. Needless to note, it is also possible to provide a transparent adhesive resin layer on the surface of the optical base material.

In a case of producing a photochromic lens by a binder method, first, a photochromic sheet is prepared by sheet formation using the photochromic curable composition. This sheet is sandwiched between two transparent sheets (optical sheets) and subjected to the polymerization as described above, whereby a photochromic laminate having the photochromic layer as an adhesive layer is obtained.

In this case, the photochromic sheet can also be prepared by coating a coating liquid containing the photochromic curable composition dissolved in an organic solvent.

The thus produced photochromic laminate is mounted in a mold, for instance, and thereafter, a thermoplastic resin (e.g., polycarbonate) for an optical base material like a lens is injection-molded, whereby a photochromic optical article having a predetermined shape like a lens and having a photochromic laminate thereon is obtained. This photochromic laminate can also be made to adhere to the surface of the optical base material by an adhesive or the like to obtain a photochromic optical article.

In a case of producing a photochromic laminate in the aforementioned manner, it is preferable that a urethane- or urea-based polymerizable compound is used as the polymerizable compound, since it has particularly high adhesion to the optical base material. Particularly preferably, a urethane-based polymerizable compound is used, which is adjusted to form polyurethane.

The aforementioned photochromic optical article obtained by polymerizing the photochromic curable composition of the present invention exhibits photochromic properties excellent in color optical density at high temperature.

The photochromic optical article obtained by polymerizing the photochromic curable composition of the present invention may be subjected to any post-treatment, depending on its application. Examples of the post-treatment include: dyeing with a dyestuff such as a dispersive dye; formation of a hard coat film by use of a silane coupling agent or a hard coat agent based on a sol of silicon, zirconium, antimony, aluminum, tin, or tungsten; formation of a thin film by vapor deposition of a metal oxide such as $SiO_2$, $TiO_2$, or $ZrO_2$; an antireflection treatment by use of a thin film coating of an organic polymer; and an antistatic treatment.

EXAMPLES

Hereinafter, the present invention will be described in detail by referring to Examples and Comparative Examples, though the present invention is not limited to the Examples. Production of the photochromic cyclic compound of the present invention in Examples will be described for each step. The number for each step is not common among these Examples.

Example 1

First Step:

| | |
|---|---|
| Hydroquinone | 110.0 g (1000 mmol), |
| potassium carbonate | 30.4 g (220 mmol), and |
| N,N-dimethylformamide | 400 mL |

were mixed, and the mixture was heated to 80° C., to which 200 mL of an N,N-dimethylformamide solution of 50.3 g (100 mmol) of the compound represented by Formula (11) below was introduced dropwise over 1 hour, and the mixture was heated at 80° C.

[CF 31]

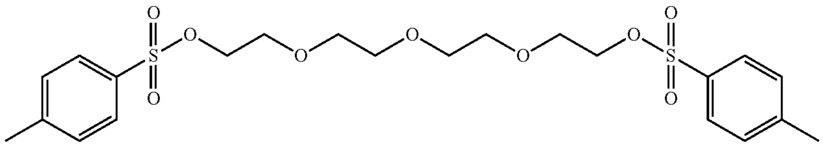

(11)

After completion of the reaction, a 5% aqueous hydrochloric acid solution was added to adjust the pH to 5. Thereafter, 5000 mL of water and 2000 mL of chloroform were added thereto and separation was performed. Washing with water was repeatedly conducted until the aqueous layer became neutral, and then, the solvent was removed and purification was performed by chromatography on silica gel, thereby obtaining a compound represented by Formula (12) below in a yield of 80%.

[CF 32]

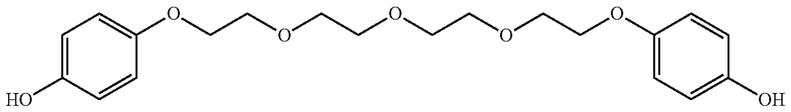

(12)

Second Step:

| | |
|---|---|
| 4,4-difluorobenzophenone | 4.4 g (20 mmol), |
| First step product (Formula 12) | 7.6 g (20 mmol), |
| dimethylacetamide | 4800 mL, |
| toluene | 1800 mL, and |
| potassium carbonate | 26.5 g (192 mmol) |

were mixed and heated to 140° C. Every time consumption of the raw materials was confirmed, 4.4 g (20 mmol) of 4,4-difluorobenzophenone and 7.6 g (20 mmol) of the First step product (Formula 12) were added. The addition was made three times.

After completion of the reaction, filtration was performed, and the solvent of the filtrate was distilled off. Purification was performed by chromatography on silica gel, thereby obtaining a compound represented by Formula (13) below in a yield of 60%.

[CF 33]

(13)

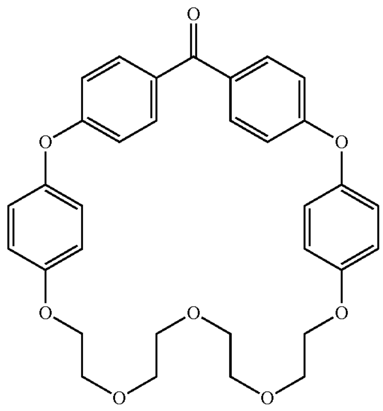

Third Step:

| | |
|---|---|
| Trimethylsilylacetylene | 1.8 g (18.0 mmol), and |
| tetrahydrofuran | 15 mL |

were mixed and stirred. After cooling to −20° C., 11.2 mL of n-BuLi (1.6 mmol/L hexane solution) was slowly added thereto, and the mixture was stirred for 1 hour.

15 mL of a tetrahydrofuran solution of 5.0 g (9.0 mmol) of the Second step product (Formula 13) was added thereto, and the mixture was stirred for 3 hours while raising the temperature to room temperature. After confirming consumption of the raw materials, ice-cooling was performed, a 10 mL methanol solution of 1.0 g (18.0 mmol) of potassium hydroxide was added, and stirring was performed for further 3 hours. After completion of the reaction, separation was performed using a 10% aqueous ammonium chloride solution, thereby obtaining a cyclic propargyl alcohol represented by Formula (14) below in a yield of 90%.

[CF 34]

(14)

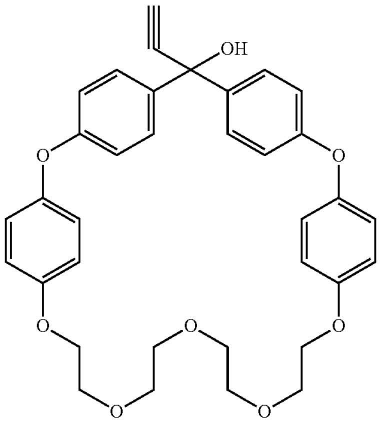

Fourth Step:

Naphthol compound of Formula (15) below 1.6 g (3.0 mmol), and cyclic propargyl alcohol compound obtained in Third step (Formula 14) 2.1 g (3.6 mmol) were dissolved in 50 ml of toluene, to which 0.75 g (0.3 mmol) of pyridinium p-toluenesulfonate was added and stirred at 85° C. for 1 hour.

[CF 35]

(15)

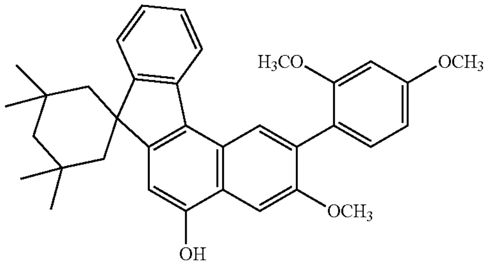

After the reaction, the solvent was removed and purification was performed by chromatography on silica gel, thereby obtaining a compound represented by Formula (16) below in a yield of 63%.

[CF 36]

(16)

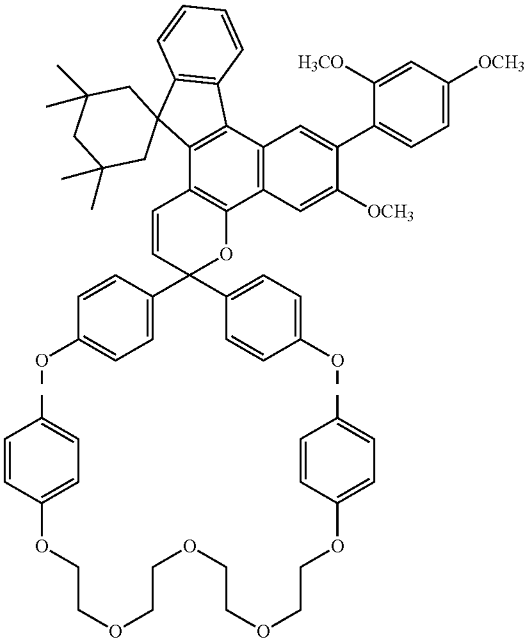

For the obtained compound, the proton nuclear magnetic resonance spectrum was measured. The following peaks were observed:

a peak of 18 H due to cyclohexane rings and methyl groups at around δ 1.0 to 3.0 ppm;

a peak of 25 H due to methoxy groups, ethyleneoxy groups at around δ 3.0 to 5.0 ppm; and a peak of 27 H due to aromatic protons and alkene protons at around δ 5.0 to 9.0 ppm.

Furthermore, the $^{13}$C-nuclear magnetic resonance spectrum was measured. The following peaks were observed:

a peak due to carbons of aromatic rings at around δ 110 to 160 ppm;

a peak due to carbons of alkenes at around δ 80 to 140 ppm; and a peak due to carbons of alkyls at δ 20 to 60 ppm.

Example 2

First Step:

A reaction was performed similarly to that of the Second step in Example 1 except that dibromododecane was used in place of the equivalent mole of the compound of Formula (12). The resultant was subjected to a subsequent reaction similarly to the Third step of Example 1, thereby obtaining a cyclic propargyl alcohol represented by Formula (17) below in a yield of 90%.

[CF 37]

(17)

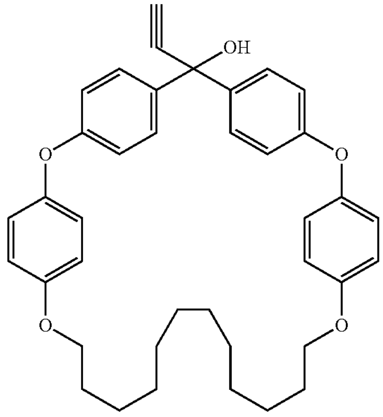

Second Step:

A reaction was performed similarly to that of the Fourth step in Example 1 except that a naphthol compound represented by Formula (18) below was used in place of the equivalent mole of the naphthol compound of Formula (15), and a cyclic propargyl alcohol (Formula 17) as the First step product was used in place of the equivalent mole of the cyclic propargyl alcohol of Formula (14), thereby obtaining a compound represented by Formula (19) below in a yield of 66%.

[CF 38]

(18)

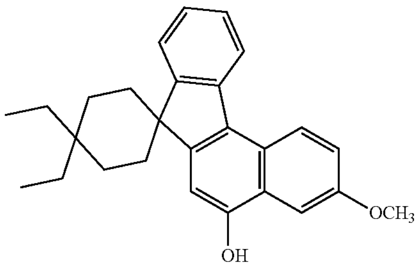

-continued

[CF 39]

(19)

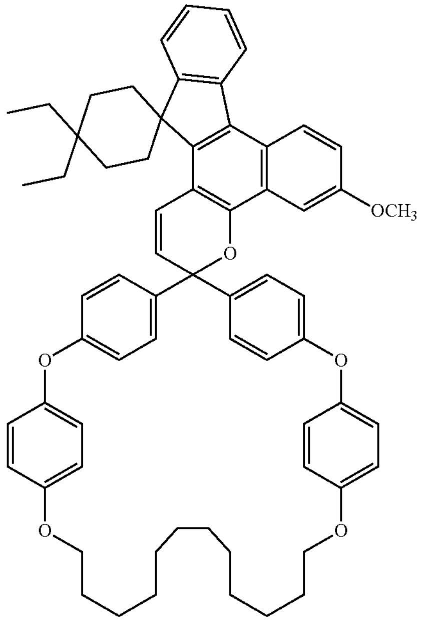

For the obtained compound, the proton nuclear magnetic resonance spectrum was measured. The following peaks were observed:

a peak of 38 H due to cyclohexyl groups, ethyl groups, dodecyl groups at around δ 1.0 to 3.0 ppm;

a peak of 7 H due to methoxy groups, dodecyl groups at around δ 3.0 to 5.0 ppm; and a peak of 25 H due to aromatic protons and alkene protons at around δ 5.0 to 9.0 ppm.

Further, the $^{13}C$-nuclear magnetic resonance spectrum was measured. The following peaks were observed:

a peak due to carbons of aromatic rings at around δ 110 to 160 ppm;

a peak due to carbons of alkenes at around δ 80 to 140 ppm; and a peak due to carbons of alkyls at δ 20 to 60 ppm.

Example 3

First Step:

| | |
|---|---|
| Hydroquinone | 110.0 g (1000 mmol), |
| potassium carbonate | 30.4 g (220 mmol), |
| 4,4-difluorobenzophenone | 21.8 g (100 mmol), and |
| N,N-dimethylformamide | 400 mL |

were mixed, and the mixture was heated to 80° C.

After completion of the reaction, the mixture was cooled to room temperature, poured into 5 L of water, and stirred overnight. After discarding the supernatant, 2 L of water was charged and reflux was performed. At room temperature, a pale brown solid was filtered to obtain a compound represented by Formula (20) below in a yield of 83%.

[CF 40]

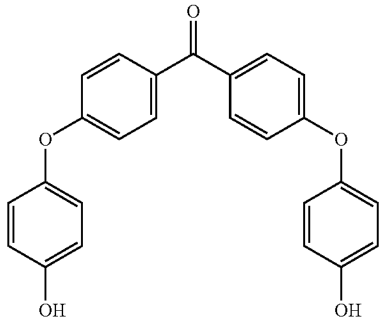

(20)

Second Step:

A reaction was performed similarly to that of the Second step in Example 1 except that difluorophenyl ether was used in place of the equivalent mole of Formula (12), and the First step product (Formula 20) was used in place of the equivalent mole of the 4,4-difluorobenzophenone, thereby obtaining a compound represented by Formula (21) below in a yield of 35%.

[CF 41]

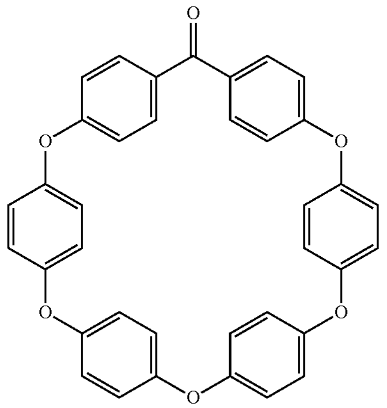

(21)

Third Step:

A reaction was performed similarly to that of the Third step in Example 1 except that the Second step product (Formula 21) was used in place of the equivalent mole of the compound of Formula (13), thereby obtaining a cyclic propargyl alcohol represented by Formula (22) below in a yield of 85%.

[CF 42]

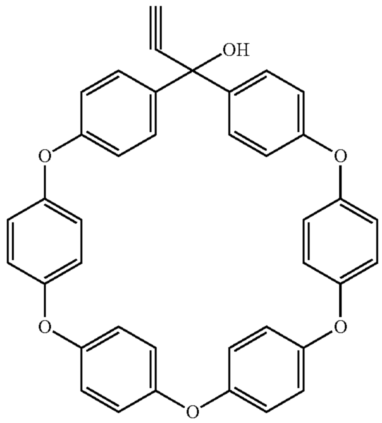

(22)

Fourth Step:

A reaction was performed similarly to that of the Fourth step in Example 1 except that a naphthol compound represented by Formula (23) below was used in place of the equivalent mole of the naphthol compound of Formula (15), and the cyclic propargyl alcohol as the Third step product (Formula 22) was used in place of the equivalent mole of the cyclic propargyl alcohol of Formula (14), thereby obtaining a compound represented by Formula (24) below in a yield of 66%.

[CF 43]

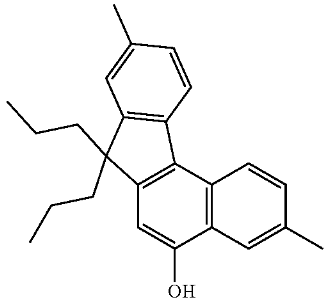

(23)

[CF 44]

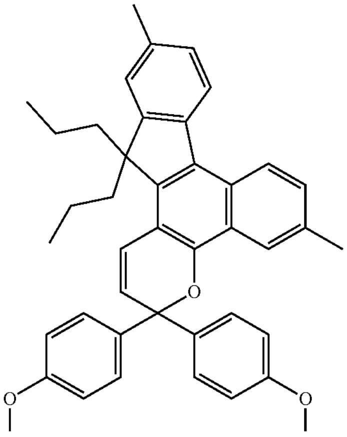

(24)

-continued

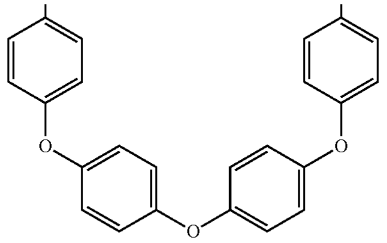

For the obtained compound, the proton nuclear magnetic resonance spectrum was measured. The following peaks were observed:

a peak of 20 H due to propyl groups, methyl groups at around δ 1.0 to 3.0 ppm; and a peak of 32 H due to aromatic protons and alkene protons at around δ 5.0 to 9.0 ppm.

Further, the $^{13}C$-nuclear magnetic resonance spectrum was measured. The following peaks were observed:

a peak due to carbons of aromatic rings at around δ 110 to 160 ppm;

a peak due to carbons of alkenes at around δ 80 to 140 ppm; and a peak due to carbons of alkyls at δ 20 to 60 ppm.

Example 4

First Step:

| | |
|---|---|
| Trimethylsilylacetylene | 17.7 g (180.0 mmol), and |
| THF | 150 mL |

were mixed, and the mixture was stirred and cooled to −20° C. Then, 112 mL of n-BuLi (1.6 mol/L hexane solution) was slowly added thereto and stirred for 1 hour.

To this mixture, a 150 mL THF solution of 13.0 g (15.0 mmol) of cyclic benzophenone represented by Formula (26) below was added, and the mixture was stirred for 10 hours while raising the temperature to room temperature.

[CF 45]

(26)

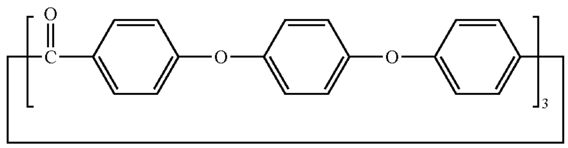

After confirming consumption of the raw materials, ice-cooling was performed, a 100 mL methanol solution of 10.0 g (180.0 mmol) of potassium hydroxide was added, and stirring was performed for further 3 hours. After completion of the reaction, separation was performed using a 10% aqueous ammonium chloride solution, thereby obtaining a cyclic propargyl alcohol represented by Formula (27) below in a yield of 90%.

[CF 46]

(27)

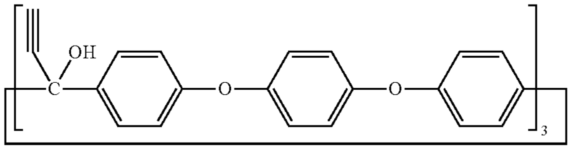

Second Step:

A naphthol compound represented by Formula (28) below was prepared.

[CF 47]

(28)

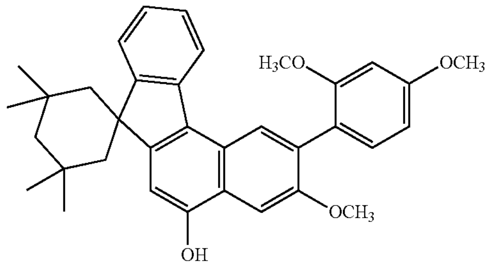

Naphthol compound of Formula (28) 1.6 g (3.0 mmol), and the cyclic propargyl alcohol of Formula (27) obtained in the First step 1.3 g (1.4 mmol) were dissolved in 50 ml of toluene, to which 0.75 g (0.3 mmol) of p-toluene-sulfonic acid pyridinium was further added, and stirred at 85° C. for 1 hour.

After the reaction, the solvent was removed and purification was performed by chromatography on silica gel, thereby obtaining a cyclic photochromic compound represented by Formula (29) below in a yield of 63%.

[CF 48]

(29)

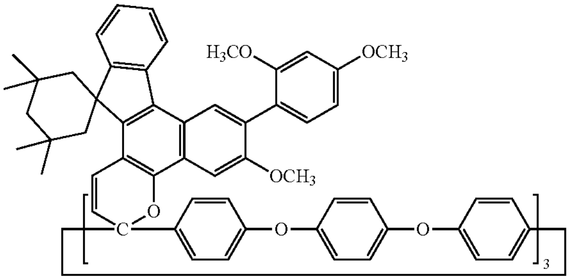

For the obtained compound, the proton nuclear magnetic resonance spectrum was measured. The following peaks were observed:

a peak of 54 H due to cyclohexane rings and methyl groups at around δ 1.0 to 3.0 ppm;

a peak of 27 H due to methoxy groups at around δ 3.0 to 5.0 ppm; and a peak of 69 H due to aromatic protons and alkene protons at around δ 5.0 to 9.0 ppm.

Further, the $^{13}$C-nuclear magnetic resonance spectrum was measured. The following peaks were observed:

a peak due to carbons of aromatic rings at around δ 110 to 160 ppm;

a peak due to carbons of alkenes at around δ 80 to 140 ppm; and a peak due to carbons of alkyls at δ 20 to 60 ppm.

Example 5

First Step:

A compound represented by Formula (30) below was prepared.

[CF 49]

(30)

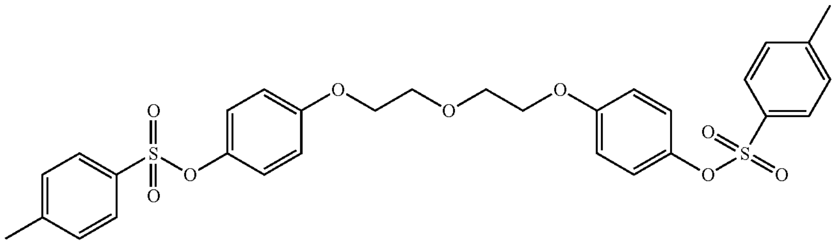

| | |
|---|---|
| the Compound of Formula (30) | 59.9 g (100 mmol), |
| potassium carbonate | 30.4 g (220 mmol), |
| 4-fluoro-4-hydroxybenzophenone | 43.2 g (200 mmol), and |
| DMF | 500 mL |

were mixed and heated to 80° C.

After completion of the reaction, the mixture was ice-cooled, and separation was performed with 3000 mL of water and 5000 mL of toluene. Washing with water was conducted repeatedly until the aqueous layer became neutral, and then, the solvent was removed and purification was performed by chromatography on silica gel, thereby obtaining a compound represented by Formula (31) below in a yield of 85%.

[CF 50]

(31)

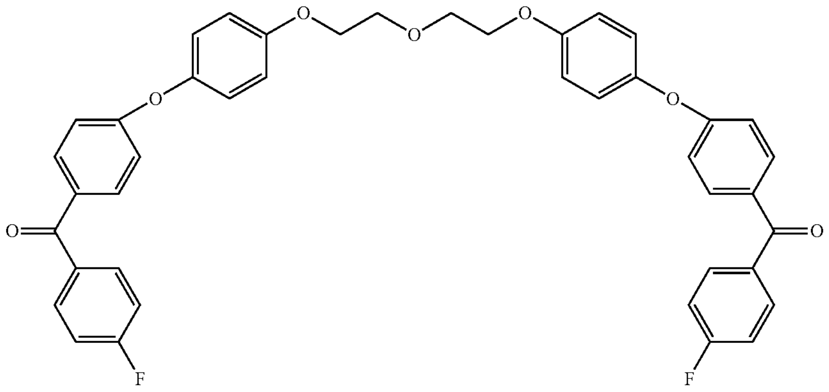

Second Step:

| | |
|---|---|
| Hydroquinone | 110.0 g (1000 mmol), |
| potassium carbonate | 30.4 g (220 mmol), and |
| DMF | 400 mL |

were mixed and heated to 80° C. To this mixture, 200 mL DMF solution of 59.9 g (100 mmol) of the compound represented by Formula (31) was added dropwise over 1 hour, and the mixture was heated at 80° C.

After completion of the reaction, a 5% aqueous hydrochloric acid solution was added to adjust the pH to 5. Then, 5000 mL of water, 2000 mL of toluene, and 1000 mL of THF were added to perform separation.

Washing with water was conducted repeatedly until the aqueous layer became neutral, and then, the solvent was removed and purification was performed by chromatography on silica gel, thereby obtaining a compound represented by Formula (32) below in a yield of 80%.

[CF 51]

(32)

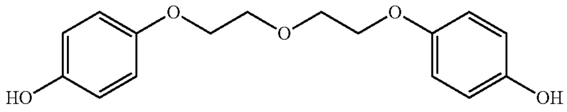

Third Step:

| | |
|---|---|
| the First step product represented by Formula (31) | 13.7 g (20 mmol), |
| the Second step product represented by Formula (32) | 5.8 g (20 mmol), |
| dimethylacetamide | 4800 mL, |
| toluene | 1800 mL, and |
| potassium carbonate | 26.5 g (192 mmol) |

were mixed and heated to 140° C. Every 12 hours, 13.7 g (20 mmol) of the First step product and 5.8 g (20 mmol) of the Second step product were added.

After completion of the reaction, filtration was performed, and the solvent of the filtrate was distilled off. Purification was performed by chromatography on silica gel, thereby obtaining a compound represented by Formula (33) below in a yield of 30%.

[CF 52]

(33)

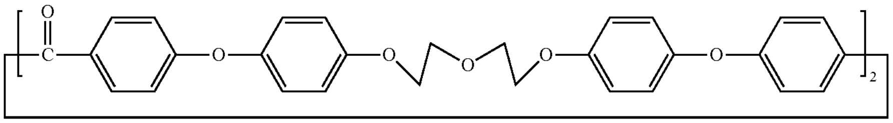

Fourth Step:

A reaction was performed similarly to that of the First step in Example 4, using the compound represented by Formula (33), thereby obtaining a cyclic propargyl alcohol represented by Formula (34) below in a yield of 87%.

[CF 53]

(34)

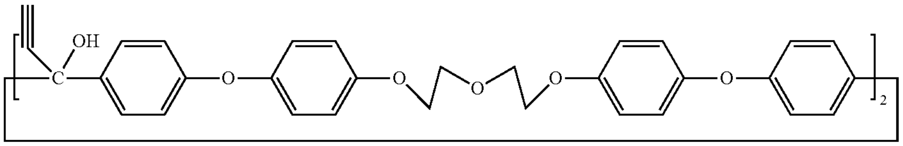

Fifth Step:

A naphthol compound represented by Formula (35) below was prepared.

[CF 54]

(35)

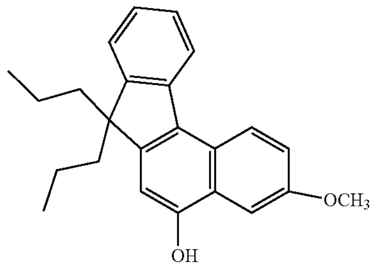

A reaction was performed similarly to that of the Second step in Example 4, except that the naphthol compound of Formula (35) was used in place of the naphthol compound represented by Formula (28), and the cyclic propargyl alcohol as the Fourth step product represented by Formula (34) was used in place of the cyclic propargyl alcohol represented by Formula (27), thereby obtaining a cyclic photochromic compound represented by Formula (36) below in a yield of 66%.

Example 6

The First Step:

| | |
|---|---|
| Hydroquinone | 110.0 g (1000 mmol), and |
| imidazole | 27.2 g (400 mmol) |

were dissolved in 280 mL of DMF and ice-cooled. To this solution, 20.3 g (100 mmol) of 1,3-dichloro-1,1,3,3-tetramethyldisiloxane dissolved in 100 mL of DMF was slowly added dropwise over 2 hours. This was made react for 12 hours while raising the temperature to room temperature.

After the reaction, separation was performed using 1000 mL of water and 500 mL of toluene. The solvent was removed and purification was performed by chromatography on silica gel, thereby obtaining a compound represented by Formula (37) below in a yield of 90%.

[CF 55]

(36)

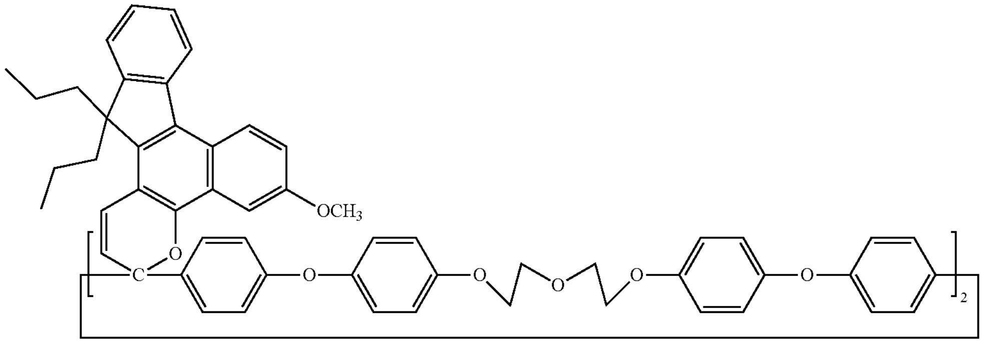

For the obtained compound, the proton nuclear magnetic resonance spectrum was measured. The following peaks were observed:

- a peak of 28 H due to propyl groups at around δ 1.0 to 3.0 ppm;
- a peak of 22 H due to methoxy groups and ethylenedioxy groups at around δ 3.0 to 5.0 ppm; and
- a peak of 50 H due to aromatic protons and alkene protons at around δ 5.0 to 9.0 ppm.

Further, the $^{13}$C-nuclear magnetic resonance spectrum was measured. The following peaks were observed:

- a peak due to carbons of aromatic rings at around δ 110 to 160 ppm;
- a peak due to carbons of alkenes at around δ 80 to 140 ppm; and
- a peak due to carbons of alkyls at δ 20 to 60 ppm.

[CF 56]

(37)

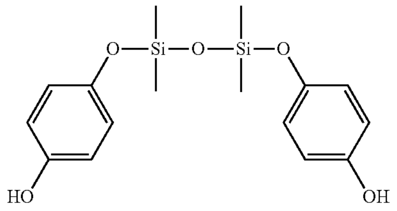

Second Step:

| | |
|---|---|
| 4-fluoro-(4-(4-hydroxyphenoxy))benzophenone | 30.8 g (100 mmol), and |
| imidazole | 13.6 g (200 mmol) |

were dissolved in 400 mL of DMF and ice-cooled. To this solution, 10.2 g (50 mmol) of 1,3-dichloro-1,1,3,3-tetramethyldisiloxane dissolved in 50 mL of DMF was slowly added dropwise over 2 hours. This was made react for 12 hours while raising the temperature to room temperature.

After the reaction, separation was performed using 300 mL of water and 500 mL of toluene. The solvent was removed and purification was performed by chromatography on silica gel, thereby obtaining a compound represented by Formula (38) below in a yield of 80%.

[CF 57]

(38)

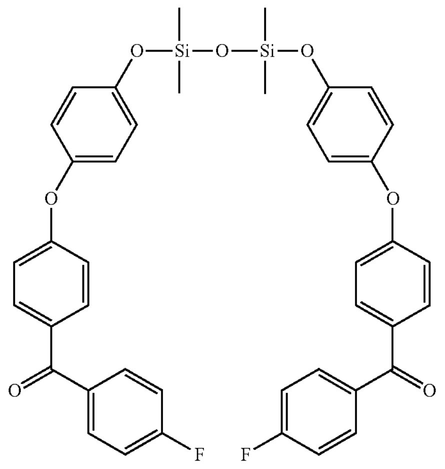

Third Step:

A reaction was performed similarly to that of the Third step in Example 5, except that the compound represented by Formula (38) was used in place of the First step product represented by Formula (31), and the compound represented by Formula (37) was used in place of the Second step product represented by Formula (32), thereby obtaining a compound represented by Formula (39) below in a yield of 20%.

[CF 58]

(39)

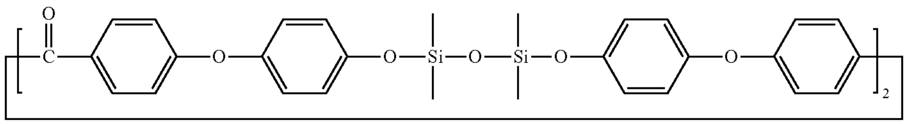

Fourth Step:

A reaction was performed similarly to that of the First step in Example 4 by using the compound represented by Formula (39), thereby obtaining a cyclic propargyl alcohol represented by Formula (40) below in a yield of 80%.

[CF 59]

(40)

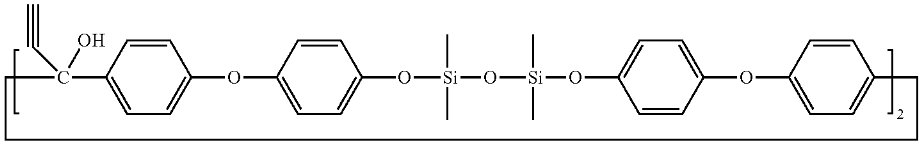

Fifth Step:

A naphthol compound represented by Formula (41) below was prepared.

[CF 60]

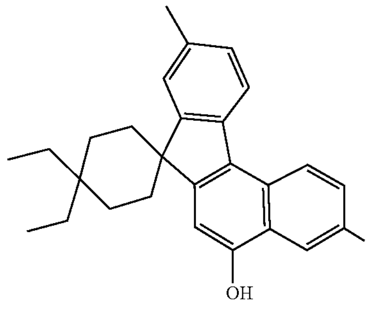

(41)

A reaction was performed similarly to that of the Second step in Example 4, except that a naphthol compound of Formula (41) was used in place of the naphthol compound represented by Formula (28), and a cyclic propargyl alcohol as the Fourth step product represented by Formula (40) was used in place of the cyclic propargyl alcohol represented by Formula (27), thereby obtaining a cyclic photochromic compound represented by Formula (42) below in a yield of 58%.

[CF 61]

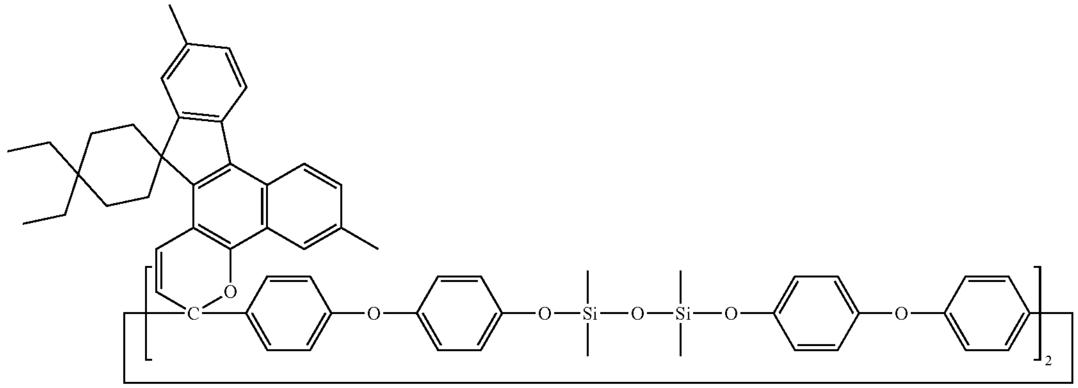

(42)

For the obtained compound, the proton nuclear magnetic resonance spectrum was measured. The following peaks were observed:

a peak of 72 H due to dimethylsiloxy groups, ethyl groups, cyclohexyl rings, methyl groups at around δ 0.0 to 3.0 ppm; and a peak of 48 H due to aromatic protons and alkene protons at around δ 5.0 to 9.0 ppm.

Furthermore, the $^{13}$C-nuclear magnetic resonance spectrum was measured. The following peaks were observed:

a peak due to carbons of aromatic rings at around δ 110 to 160 ppm;

a peak due to carbons of alkenes at around δ 80 to 140 ppm; and a peak due to carbons of alkyls and carbons of siloxanes at δ 0 to 60 ppm.

[Method for Evaluating Photochromic Cyclic Compound]

Toluene solutions were prepared so that the compounds of Examples or Comparative Examples described below each would be 1 mmol/L in terms of photochromic basic structural group PC, and the solutions were subjected to the following evaluation using a quartz cell with an optical path length of 1 cm. For instance, since the compound of Example 4 has three photochromic basic structural groups PC (naphthopyran basic structural group), a prepared toluene solution would be 0.33 mmol/L. The results are shown in Table 1.

(1)Photochromic Property

[1] Maximum Absorption Wavelength (λmax):

The maximum absorption wavelength was obtained after color development by a spectrophotometer (instantaneous multichannel photodetector, MCPD3000) manufactured by Otsuka Electronics Co., Ltd. for use as an indicator of the color tone at the time of color development.

[2] Color Optical Density ($A_{23}$) at 23° C.:

A difference between the absorbance {ε(180)} after light irradiation at 23° C. for 180 seconds and the absorbance ε(0) before light irradiation, at the aforementioned maximum absorption wavelength, was defined as an indicator of the color optical density. The higher this value, the better the photochromic properties.

[3] Color Optical Density ($A_{35}$) at 35° C.:

A difference between the absorbance {ε(180)} after light irradiation at 35° C. for 180 seconds and the absorbance ε(0) before light irradiation, at the aforementioned maximum absorption wavelength, was defined as an indicator of the color optical density. The higher this value, the better the photochromic properties.

[4] Temperature Dependence ($A_{35}/A_{23}$×100):

A ratio of the color optical density ($A_{35}$) at 35° C. to the color optical density ($A_{23}$) at 23° C. was defined as temperature dependence. The higher this value, the smaller and better the temperature dependence.

[5] Fading Half-Life at 23° C. [τ1/2 (Sec.)]:

A time required for the absorbance of the sample at the aforementioned maximum absorption wavelength to decrease to ½ of {ε(180)−ε(0)} when light irradiation at 23° C. for 180 seconds was stopped was defined as an indicator of the fading rate. The shorter this time, the higher the fading rate.

Comparative Examples 1-2

For comparison, toluene solutions of 1.0 mmol/L of photochromic compounds represented by Formulas (A) and (B) below were obtained and subjected to the property evaluation in the same manner as in Examples. The results are shown in Table 1.

[CF 62]

(A)

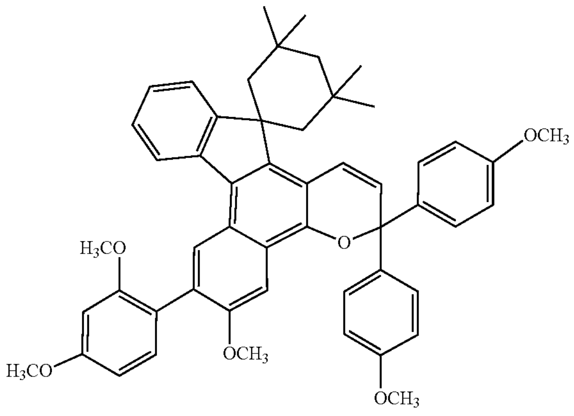

-continued (B)

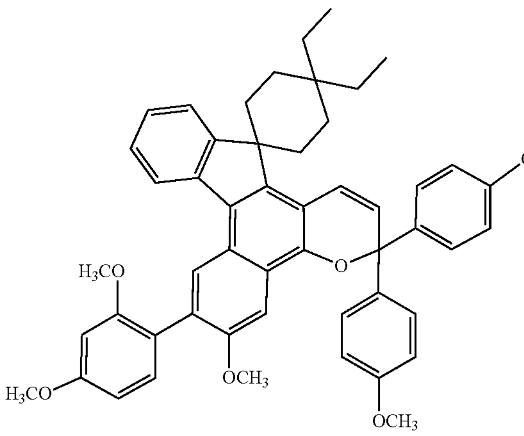

Since the photochromic cyclic compounds used in Examples and the photochromic compounds used in Comparative Examples have two maximum absorption wavelengths in the visible light range, the color optical density at 23° C., the color optical density at 35° C., the temperature dependence and the fading half-life at 23° C. in the each maximum absorption wavelengths are indicated.

TABLE 1

| | Compound No. | Maximum absorption wavelength (nm) | Color optical density at 23° C. (—) | Color optical density at 35° C. (—) | Temperature dependence (%) | Fading half-life at 23° C. (sec) |
|---|---|---|---|---|---|---|
| Example 1 | Formula (16) | 425 | 0.74 | 0.49 | 66% | 53 |
| | | 560 | 0.65 | 0.44 | 67% | 53 |
| Example 2 | Formula (19) | 412 | 0.67 | 0.50 | 75% | 90 |
| | | 561 | 0.76 | 0.57 | 75% | 91 |
| Example 3 | Formula (24) | 424 | 0.50 | 0.31 | 61% | 67 |
| | | 543 | 0.88 | 0.58 | 67% | 67 |
| Example 4 | Formula (29) | 425 | 0.73 | 0.45 | 62% | 53 |
| | | 556 | 0.67 | 0.42 | 62% | 53 |
| Example 5 | Formula (36) | 414 | 0.50 | 0.32 | 64% | 44 |
| | | 552 | 0.66 | 0.42 | 64% | 44 |
| Example 6 | Formula (42) | 427 | 0.62 | 0.42 | 69% | 68 |
| | | 554 | 0.93 | 0.65 | 69% | 69 |
| Comparative | Formula (A) | 432 | 0.66 | 0.37 | 56% | 35 |
| Example 1 | | 564 | 0.68 | 0.38 | 56% | 36 |
| Comparative | Formula (B) | 446 | 0.79 | 0.47 | 59% | 59 |
| Example 2 | | 560 | 0.86 | 0.51 | 59% | 59 |

The FIGURE shows a plot of the results of the temperature dependence and the fading half-life at 23° C. in Example 1 and Comparative Examples 1 to 2.

As can be seen from the FIGURE, the compounds of Comparative Examples exhibit a linear relationship between the temperature dependence and the fading half-life at 23° C. This means that a compound with a higher fading rate has smaller temperature dependence.

Since the compounds of Examples and the compounds of Comparative Examples have the substantially same structures except for the presence or absence of a cyclic structure, the compound of Example 1 and the compounds of Comparative Examples 1 to 2, which are contained at the same concentration in terms of the photochromic basic structural groups, can be compared as they are. As is evident from the FIGURE, the relationship of Example 1 using the photochromic cyclic compound of the present invention is observed above the linear relationship of Comparative Examples. This means that the photochromic cyclic compound of the present invention is superior (smaller) in temperature dependence when compared at the same fading rate.

(Evaluation of Photochromic Plastic Lens Produced by Coating Method)

Example 7

The photochromic cyclic compound obtained in Example 1 was mixed with a photopolymerization initiator and a polymerizable compound. Then, the mixture was coated on the surface of a lens base material, and further irradiated with ultraviolet rays to polymerize a coating film on the surface of the lens base material.

A mixture of the following components was used for the polymerizable composition.

| | |
|---|---|
| Polyethylene glycol dimethacrylate (average molecular weight: 736) | 45 parts by mass |
| Polyethylene glycol dimethacrylate (average molecular weight: 536) | 7 parts by mass |
| Trimethylolpropane trimethacrylate | 40 parts by mass |
| γ-methacryloyloxypropyltrimethoxysilane | 2 parts by mass |
| Glycidyl methacrylate | 1 part by mass |

Using the mixture of the polymerizable compound, the respective components were thoroughly mixed in accordance with the following formulation, thereby preparing a photochromic curable composition.

The total amount of the polymerizable compound was 100 parts by mass, including:

| | |
|---|---|
| photochromic cyclic compound of Example 1 | 0.27 mmol; |
| phenylbis(2,4,6-trimethylbenzoyl)phosphine oxide (photopolymerization initiator: Irgacure 819 manufactured by BASF) | 0.3 parts by mass; |
| ethylenebis(oxyethylene)bis[3-(5-tert-butyl-4-hydroxy-m-tolyl)propionate] (stabilizer: Irganox 245 manufactured by Ciba Specialty Chemicals) | 1 part by mass; |
| bis(1,2,2,6,6-pentamethyl-4-piperidyl) sebacate (molecular weight: 508) | 3 parts by mass; and |
| leveling agent (L7001 manufactured by Toray Dow Corning Corp.) | 0.1 parts by mass. |

Then, a thiourethane-based plastic lens having a center thickness of 2 mm and a refractive index of 1.60 was used as the optical base material.

This thiourethane-based plastic lens was subjected in advance to alkali etching at 50° C. for five minutes using a 10% aqueous sodium hydroxide solution, and then, washed sufficiently with distilled water.

A spin coater (1H-DX2 manufactured by MIKASA Corporation) was used to spin-coat a moisture-curable primer (product name: TR-SC-P, manufactured by Tokuyama Corporation) on the surface of the aforementioned thiourethane-based plastic lens for 15 seconds at a rotational speed of 70 rpm, and then, for 10 seconds at 1000 rpm. Thereafter, 2 g of the obtained photochromic curable composition was spin-coated for 40 seconds at a rotational speed of 60 rpm, and then, for 10 to 20 seconds at 600 rpm so that the coating layer had a film thickness of 40 μm.

The thiourethane-based plastic lens thus coated with the photochromic curable composition thereon was irradiated with light for 90 seconds by using a metal halide lamp having a power of 200 mW/$cm^2$ in a nitrogen gas atmosphere to polymerize the photochromic curable composition, which was later heated at 110° C. further for one hour to produce a photochromic optical article.

The thus obtained photochromic optical article was evaluated in the same manner as in Examples 1 to 6. The results are shown in Table 2.

Examples 8 to 12

Operations similar to those of Example 7 were carried out except for use of the compounds described in Table 2, thereby producing photochromic optical articles, which were evaluated in a like manner. The results are shown in Table 2.

TABLE 2

| | Compound No. | Maximum absorption wavelength (nm) | Color optical density at 23° C. (—) | Color optical density at 35° C. (—) | Temperature dependence (%) | Fading half-life at 23° C. (sec) |
|---|---|---|---|---|---|---|
| Example 7 | Formula (16) | 444 | 0.77 | 0.49 | 64% | 92 |
| | | 568 | 0.70 | 0.45 | 64% | 93 |
| Example 8 | Formula (19) | 437 | 0.58 | 0.39 | 67% | 99 |
| | | 560 | 0.74 | 0.50 | 68% | 100 |
| Example 9 | Formula (24) | 440 | 0.74 | 0.51 | 69% | 163 |
| | | 564 | 1.10 | 0.77 | 70% | 169 |
| Example 10 | Formula (29) | 427 | 0.46 | 0.36 | 78% | 186 |
| | | 566 | 0.41 | 0.32 | 78% | 187 |
| Example 11 | Formula (36) | 414 | 0.41 | 0.34 | 82% | 219 |
| | | 558 | 0.54 | 0.45 | 84% | 220 |
| Example 12 | Formula (42) | 426 | 0.31 | 0.23 | 74% | 163 |
| | | 540 | 0.54 | 0.39 | 72% | 162 |

As can be seen from Table 2, the photochromic cyclic compound of the present invention exhibits an excellent effect even for a photochromic optical article obtained by polymerizing the photochromic curable composition containing the photochromic cyclic compound, similarly to a case where it is in the toluene solution.

Example 13

First Step:

| | |
|---|---|
| 4,4-dihydroxybenzophenone | 21.4 g (100 mmol), and |
| dibromododecane | 32.8 g (100 mmol) |

were dissolved in 3000 mL of dimethylformamide, which was slowly added dropwise into a dimethylformamide solution (6000 mL) of 20.1 g (150 mmol) of potassium carbonate that had been heated to 90° C. After completion of the reaction, 10000 mL of water and 5000 mL of chloroform were added to the solution, and separation was performed. Washing with water was repeated four times to distill the solvent off. Purification was performed by chromatography on silica gel, thereby obtaining a compound represented by Formula (43) below in a yield of 20%.

[CF 63]

(43)

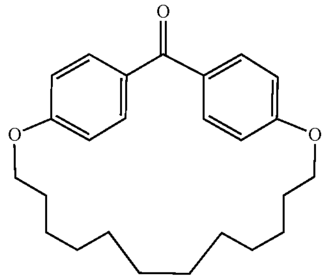

Second Step:

A reaction was performed similarly to that of the Third step in Example 1, thereby obtaining a cyclic propargyl alcohol represented by Formula (44) below in a yield of 86%.

[CF 64]

(44)

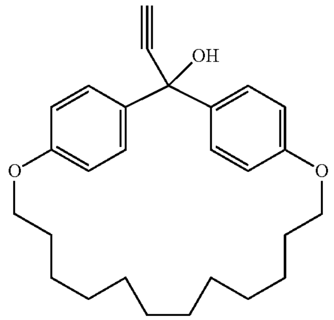

Third Step:

A reaction was performed similarly to that of the Fourth step in Example 1, except that a naphthol compound represented by Formula (45) below was used in place of the equivalent mole of the naphthol compound of Formula (15), and the cyclic propargyl alcohol (44) as the Second step product was used in place of the equivalent mole of the cyclic propargyl alcohol of Formula (14), thereby obtaining a compound represented by Formula (46) below in a yield of 62%.

[CF 65]

(45)

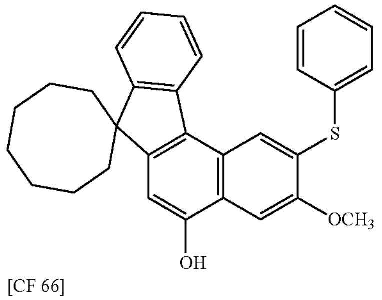

[CF 66]

(46)

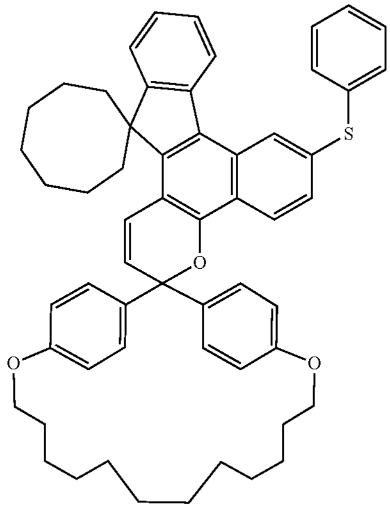

For the obtained compound, the proton nuclear magnetic resonance spectrum was measured. The following peaks were observed:

- a peak of 34 H due to cyclooctyl groups, dodecyl groups at around δ 1.0 to 3.0 ppm;
- a peak of 7 H due to methoxy groups, dodecyl groups at around δ 3.0 to 5.0 ppm; and
- a peak of 21 H due to aromatic protons and alkene protons at around δ 5.0 to 9.0 ppm.

Example 14

First Step:

| | |
|---|---|
| 4-(hydroxymethyl)cyclohexanol | 25 g (192 mmol), and |
| imidazole | 26.3 g (384 mmol) |

were dissolved in 200 mL of THF and the solution was ice-cooled, to which 28.9 g (192 mmol) of dimethyl tertiary butyl chlorosilane was slowly added dropwise. After completion of the reaction, filtration was performed to concentrate the solvent of the filtrate. Purification was performed by chromatography on silica gel, thereby obtaining 4-(dimethyltertiary butylsilyloxymethyl)cyclohexanol in a yield of 86%.

Second Step:

| | |
|---|---|
| 4,4'-dihydroxybenzophenone | 8.82 g (41.2 mmol), |
| triphenylphosphine | 43.2 g (164.7 mmol), |
| 4-(dimethyltertiary butylsilyloxymethyl)cyclohexanol | 40.8 g (164.7 mmol), and |
| THF | 200 mL |

were added and ice-cooled, to which 250 mL of DIAD was slowly added dropwise. After stirring overnight, the solvent was concentrated. Purification was performed by chromatography on silica gel, thereby obtaining benzophenone represented by Formula (47) below in a yield of 91%.

[CF 67]

(47)

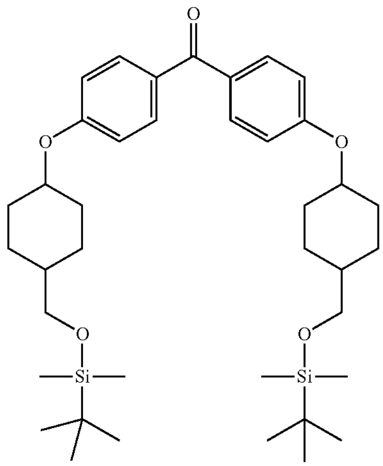

Third Step:

A reaction was performed similarly to that of the Third step in Example 1, thereby obtaining a propargyl alcohol represented by Formula (48) below in a yield of 76%.

[CF 68]

(48)

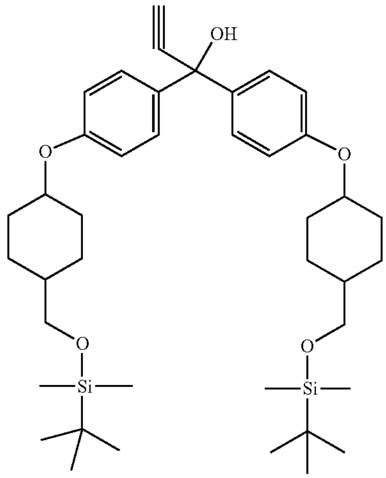

Fourth Step:

A reaction was performed similarly to that of the Fourth step in Example 1 except that a naphthol compound represented by Formula (49) below was used in place of the equivalent mole of the naphthol compound of Formula (15), and the cyclic propargyl alcohol (48) as the Second step product was used in place of the equivalent mole of the cyclic propargyl alcohol of Formula (14). After the reaction, the solvent was concentrated, and 20 mL of THF was added thereto and ice-cooled. Then, after adding 10 mL of tetrabutylammonium fluoride (1 MTHF solution), the solution was stirred. After the reaction, the organic layer was concentrated, and purification was performed by chromatography on silica gel, thereby obtaining a compound represented by Formula (50) below in a yield of 58%.

[CF 69]

(49)

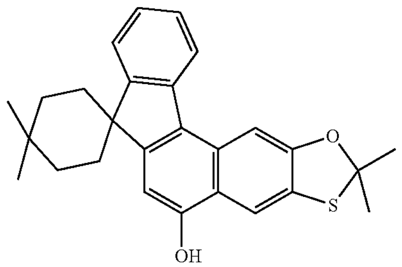

[CF 70]

(50)

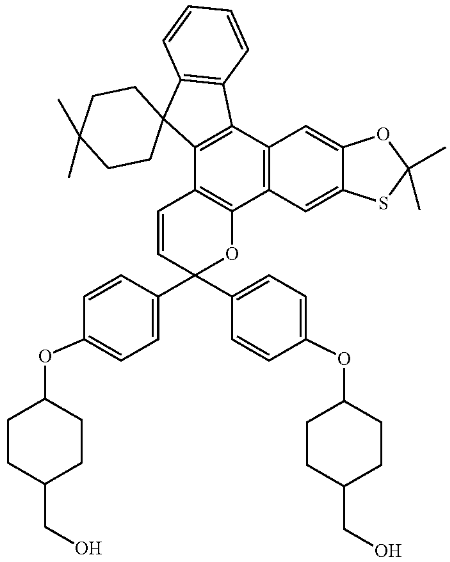

Fifth Step:

1.50 g of the compound of Formula (50) was dissolved in 20 mL of THF, to which 0.53 g (5.2 mol) of succinic anhydride was added, which was made react at room temperature for 12 hours. After the reaction, 10 mL of 10% hydrochloric acid was added, separation was performed, and the organic layer was concentrated. 2 g (33 mmol) of dimethylaminopyridine, 7.9 g (33 mmol) of WSC and 2000 mL of dichloromethane were added thereto. After ice-cooling, 0.6 g (0.4 mol) of p-xylene α,α'-diol was added. The solution was stirred at room temperature for 12 hours, ice-cooled, and 0.6 g (0.4 mol) of p-xylene-α,α'-diol was further added. Addition of p-xylene-α,α'-diol was repeated twice.

After the reaction, separation was performed, and then, the solvent was concentrated. Purification was performed by chromatography on silica gel, thereby obtaining a compound represented by Formula (51) below in a yield of 20%.

[CF 71]

(51)

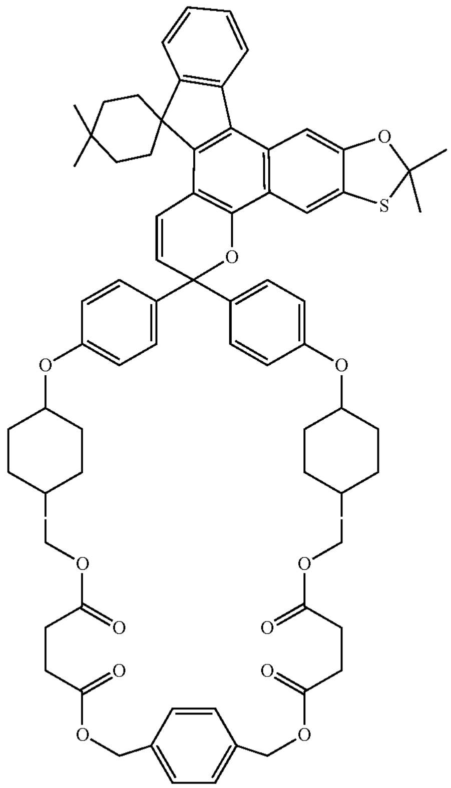

For the obtained compound, the proton nuclear magnetic resonance spectrum was measured. The following peaks were observed:

a peak of 46 H due to cyclohexyl groups, succinic groups at around δ 1.0 to 3.0 ppm;

a peak of 10 H due to cyclohexyl groups at around δ 3.0 to 5.0 ppm; and a peak of 20 H due to aromatic protons and alkene protons at around δ 5.0 to 9.0 ppm.

Example 15

First Step:

A reaction was performed similarly to that of the Fourth step in Example 14, except that a naphthol compound represented by Formula (52) below was used in place of the equivalent mole of the naphthol compound of Formula (49), thereby obtaining a compound represented by Formula (53) below in a yield of 68%.

[CF 72]

(52)

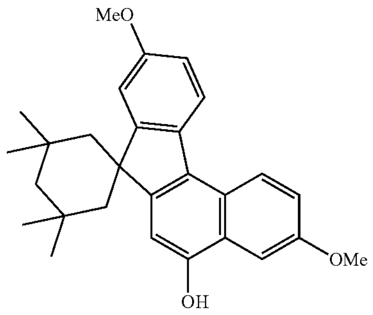

[CF 73]

(53)

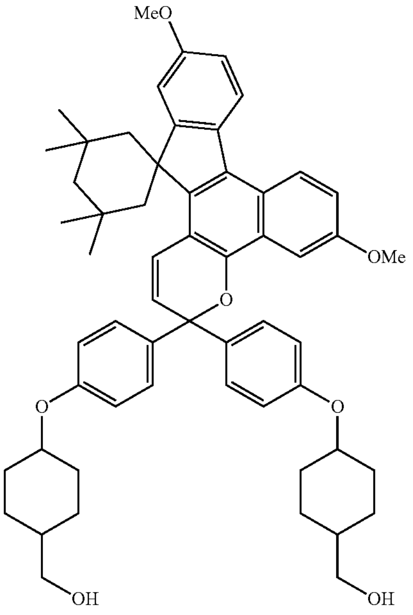

Second Step:

1.8 g (2.0 mol) of the compound of Formula (53) and 0.29 g (4.2 mol) of imidazole were dissolved in 100 mL of THF, which was then ice-cooled. To this solution, 50 mL of THF solution containing 0.7 g (2.0 mol) of 1,7-dichloro-1,1,3,3,5,5,7,7-octamethylheptanetetrasiloxane was slowly added. The solution was stirred for 3 hours under ice-cooling, and stirred overnight while slowly raising the temperature to room temperature. After the reaction, separation was performed. After solvent concentration, purification was performed by chromatography on silica gel, thereby obtaining a compound represented by Formula (54) below in a yield of 30%.

[CF 74]

(54)

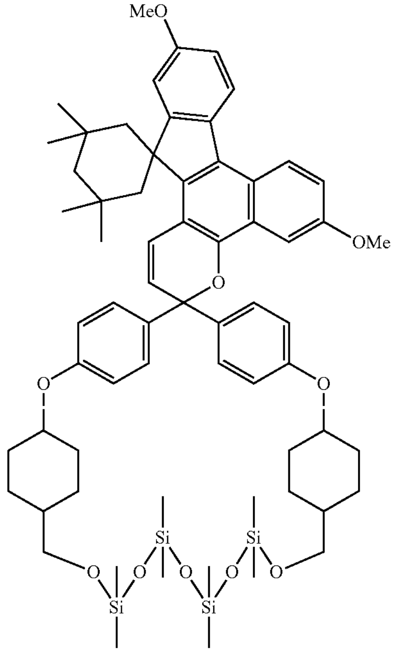

For the obtained compound, the proton nuclear magnetic resonance spectrum was measured. The following peaks were observed:

a peak of 60 H due to dimethylsilyl groups, cyclohexyl groups at around δ 0.0 to 3.0 ppm;

a peak of 12 H due to methoxy groups, cyclohexyl groups at around δ 3.0 to 5.0 ppm; and a peak of 16 H due to aromatic protons and alkene protons at around δ 5.0 to 9.0 ppm;

Example 16

First Step:

A reaction was performed similarly to that of the Second step in Example 2 except that a naphthol compound represented by Formula (55) below was used in place of the equivalent mole of the naphthol compound of Formula (18), thereby obtaining a compound represented by Formula (56) below in a yield of 57%.

[CF 75]

(55)

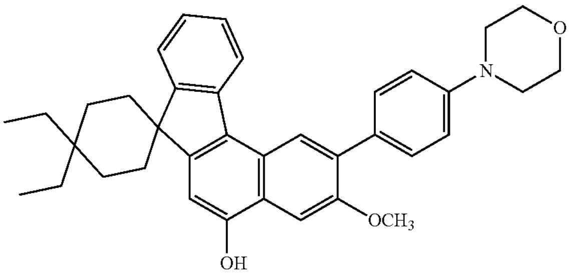

-continued

[CF 76]

(56)

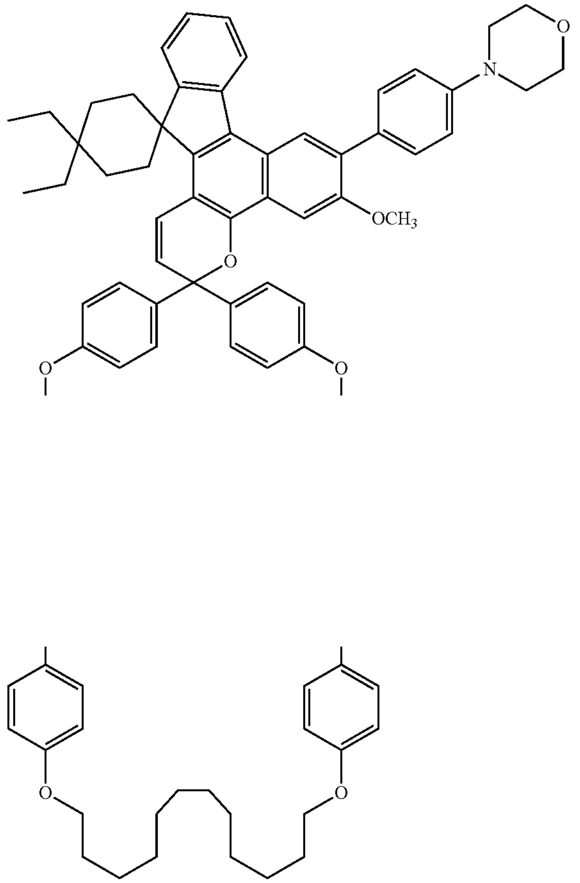

For the obtained compound, the proton nuclear magnetic resonance spectrum was measured. The following peaks were observed:

a peak of 38 H due to cyclohexyl groups, dodecyle groups at around δ 1.0 to 3.0 ppm;

a peak of 15 H due to cyclohexyl groups at around δ 3.0 to 5.0 ppm; and a peak of 28 H due to aromatic protons and alkene protons at around δ 5.0 to 9.0 ppm.

Example 17

First Step:

Operations were performed similarly to those of the First step in Example 3 except that 2 equivalents of difluorobenzene was used relative to hydroquinone in place of difluorobenzophenone, thereby obtaining 1,4-bis(p-fluorophenoxy)benzen in a yield of 50%.

Second Step:

Operations were performed similarly to those of the Second step in Example 3 except that 1,4-bis(p-fluorophenoxy)benzene was used in place of difluorophenyl ether, thereby obtaining a compound represented by Formula (57) below in a yield of 27%.

[CF 77]

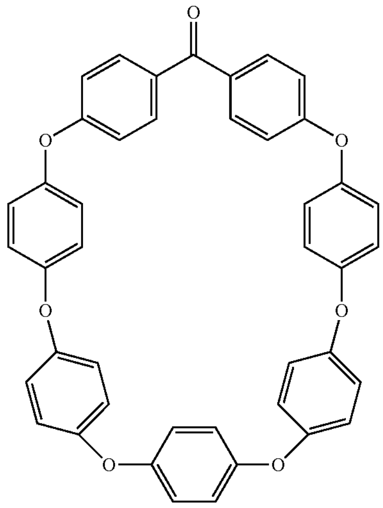

(57)

Third Step:

Operations were performed similarly to those of the Third step in Example 1 except that the Second step product (57) was used in place of the equivalent mole of the compound of Formula (13), thereby obtaining a cyclic propargyl alcohol represented by Formula (58) below in a yield of 76%.

[CF 78]

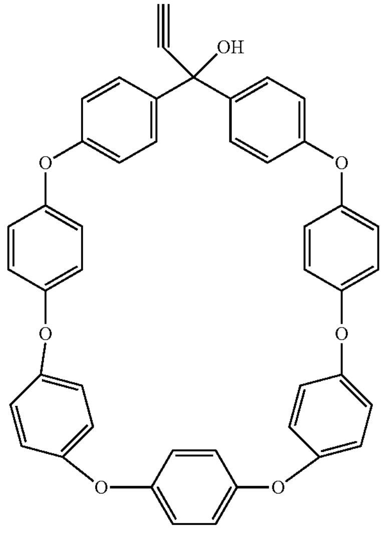

(58)

Fourth Step:

Operations were performed similarly to those of the Fourth step in Example 1 except that a naphthol compound represented by Formula (59) below was used in place of the equivalent mole of the naphthol compound of Formula (15), and a cyclic propargyl alcohol as the Third step product (Formula 58) was used in place of the equivalent mole of the cyclic propargyl alcohol of Formula (14), thereby obtaining a compound represented by Formula (60) below in a yield of 47%.

[CF 79]

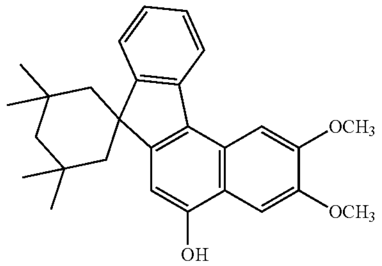

(59)

[CF 80]

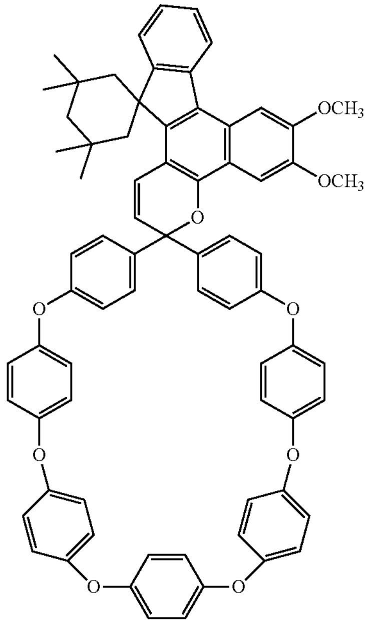

(60)

For the obtained compound, the proton nuclear magnetic resonance spectrum was measured. The following peaks were observed:

a peak of 18 H due to cyclohexyl groups at around δ 1.0 to 3.0 ppm;

a peak of 6 H due to cyclohexyl groups at around δ 3.0 to 5.0 ppm; and a peak of 36 H due to aromatic protons and alkene protons at around δ 5.0 to 9.0 ppm.

Example 18

A reaction was performed similarly to that of the First step in Example 13, except that the compound of Formula (11) was used in place of dibromododecane, thereby obtaining a compound represented by Formula (61) below in a yield of 15%.

[CF 81]

(61)

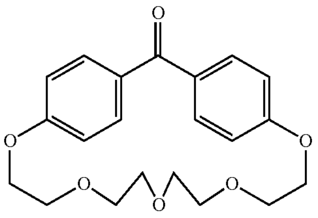

Second Step:

A reaction was performed similarly to that of the Third step in Example 1, thereby obtaining a cyclic propargyl alcohol represented by Formula (62) below in a yield of 81%.

[CF 82]

(62)

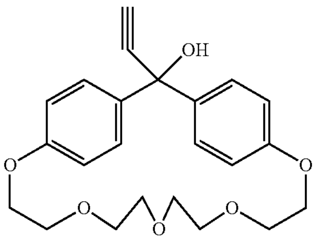

Third Step:

A reaction was performed similarly to that of the Fourth step in Example 1, except that a naphthol compound represented by Formula (63) below was used in place of the equivalent mole of the naphthol compound of Formula (15), and the cyclic propargyl alcohol (62) as the Second step product was used in place of the equivalent mole of the cyclic propargyl alcohol of Formula (14), thereby obtaining a compound represented by Formula (64) below in a yield of 66%.

[CF 83]

(63)

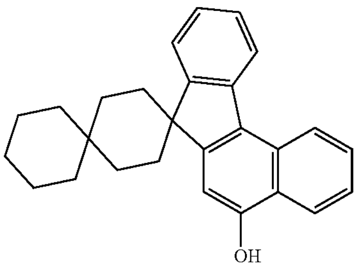

-continued

[CF 84]

(64)

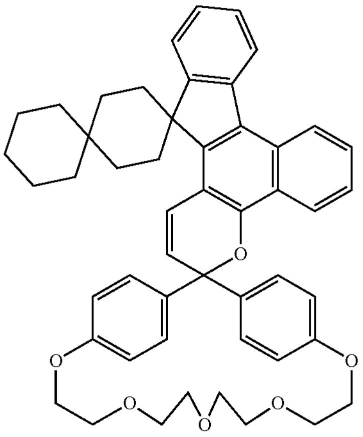

For the obtained compound, the proton nuclear magnetic resonance spectrum was measured. The following peaks were observed:

a peak of 18 H due to cyclohexyl groups at around δ 1.0 to 3.0 ppm;

a peak of 16 H due to methoxy groups, ethylene glycol groups at around δ 3.0 to 5.0 ppm; and a peak of 17 H due to aromatic protons and alkene protons at around δ 5.0 to 9.0 ppm.

Example 19

First Step:

| | |
|---|---|
| 3-bis (4-piperidyl) propane | 21.0 g (100.0 mmol), |
| 4-fluorophenol | 33.6 g (300.0 mmol), |
| triethylamine | 50.5 g (500.0 mmol), and |
| dimethyl sulfoxide | 50 mL |

were mixed and heated at 100° C. After consumption of the materials, separation was performed with 2000 mL of water and 500 mL of dichloromethane, and the organic layer was concentrated. Purification was performed by chromatography on silica gel, thereby obtaining a compound represented by Formula (65) below in a yield of 75%.

[CF 85]

(65)

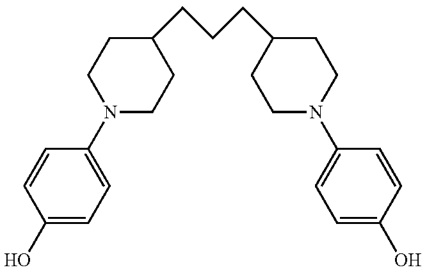

Second Step:

Procedures were performed similarly to those of the Second step in Example 1 except that the compound of Formula (65) was used in place of the compound of Formula (12). Subsequently, the thus obtained product was subjected to a reaction similar to that of the Third step in Example 1, thereby obtaining a cyclic propargyl alcohol represented by Formula (66) below in a yield of 90%.

[CF 86]

(66)

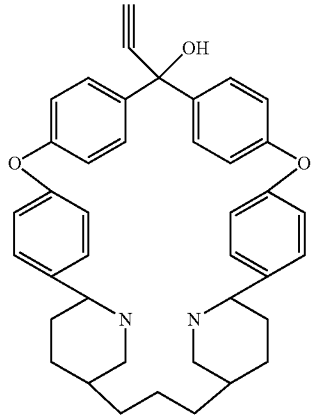

Third Step:

A reaction was performed similarly to that of the Fourth step in Example 1, except that a naphthol compound represented by Formula (67) below was used in place of the equivalent mole of the naphthol compound of Formula (15), and the cyclic propargyl alcohol (66) as the Second step product was used in place of the equivalent mole of the cyclic propargyl alcohol of Formula (14), thereby obtaining a compound represented by Formula (68) below in a yield of 54%.

[CF 87]

(67)

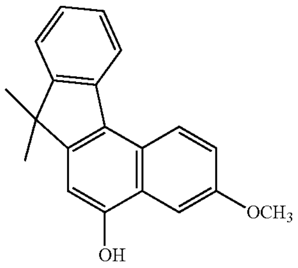

-continued

[CF 88]

(68)

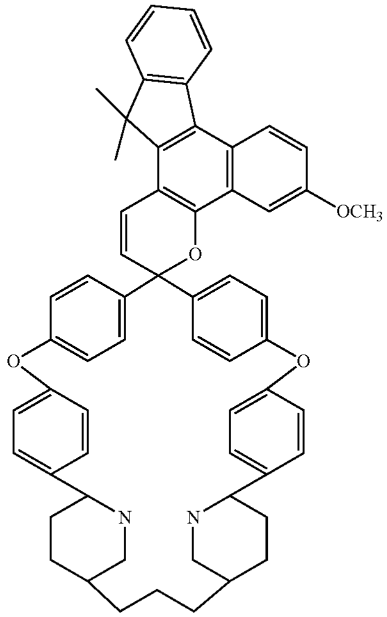

For the obtained compound, the proton nuclear magnetic resonance spectrum was measured. The following peaks were observed:

a peak of 22 H due to piperidino groups, methyl groups at around δ 1.0 to 3.0 ppm;

a peak of 11 H due to methoxy groups, piperidino groups at around δ 3.0 to 5.0 ppm; and a peak of 25 H due to aromatic protons and alkene protons at around δ 5.0 to 9.0 ppm.

Examples 20 to 26

Photochromic optical articles were produced in the same manner as in Example 7, except that the compounds described in Table 3 were used, and the same evaluation was performed. The results are shown in Table 3.

TABLE 3

| | Compound No. | Maximum absorption wavelength (nm) | Color optical density at 23° C. (—) | Color optical density at 35° C. (—) | Temperature dependence (%) | Fading half-life at 23° C. (sec) |
|---|---|---|---|---|---|---|
| Example 20 | Formula (46) | 461 | 1.36 | 0.90 | 68% | 136 |
| | | 566 | 0.94 | 0.63 | 68% | 136 |
| Example 21 | Formula (51) | 462 | 0.89 | 0.55 | 62% | 98 |
| | | 567 | 0.66 | 0.40 | 62% | 98 |
| Example 22 | Formula (54) | 464 | 0.41 | 0.26 | 65% | 94 |
| | | 595 | 0.84 | 0.54 | 65% | 95 |
| Example 23 | Formula (56) | 459 | 1.09 | 0.76 | 70% | 123 |
| | | 563 | 0.80 | 0.55 | 69% | 122 |
| Example 24 | Formula (60) | 446 | 0.72 | 0.42 | 59% | 85 |
| | | 563 | 0.43 | 0.25 | 59% | 84 |
| Example 25 | Formula (65) | 428 | 0.45 | 0.22 | 51% | 37 |
| | | 544 | 0.95 | 0.47 | 51% | 37 |

TABLE 3-continued

| | Compound No. | Maximum absorption wavelength (nm) | Color optical density at 23° C. (—) | Color optical density at 35° C. (—) | Temperature dependence (%) | Fading half-life at 23° C. (sec) |
|---|---|---|---|---|---|---|
| Example 26 | Formula (69) | 435 | 0.62 | 0.43 | 71% | 190 |
| | | 572 | 0.77 | 0.55 | 72% | 192 |

The invention claimed is:

1. A photochromic cyclic compound represented by Formula (1) below:

(1)

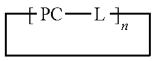

in the formula,

PC denotes a divalent T-type photochromic basic structural group, L denotes a divalent bridging group, and n is an integer of 1 or more, the PC to denote the T-type photochromic basic structural group is a naphthopyran structural group represented by Formula (2) below:

(2)

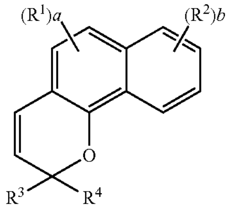

in Formula (2), provided that at least one of $R^3$ and $R^4$ is a bonding hand to the divalent bridging group L or a group having the bonding hand, $R^1$ and $R^2$ are each a group having a bonding hand to the divalent bridging group L or a group having the bonding hand, a hydroxyl group, an alkyl group, a cycloalkyl group, an alkoxy group, an amino group, a heterocyclic group, a cyano group, a halogen atom, an alkylthio group, an arylthio group, a nitro group, a formyl group, a hydroxycarbonyl group, an alkylcarbonyl group, an alkoxycarbonyl group, an aralkyl group, an aralkoxy group, an aryloxy group, an aryl group, a heteroaryl group, a thiol group, an alkoxyalkylthio group, a cycloalkylthio group, a group represented by Formula (X) below, or a group represented by Formula (Y) below:

(X)

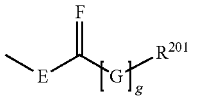

in the Formula (X),

E is an oxygen atom or $NR^{101}$, and $R^{101}$ is a hydrogen atom or an alkyl group, F is an oxygen atom or a sulfur atom, G is an oxygen atom, a sulfur atom or a $NR^{202}$, and $R^{202}$ is a hydrogen atom, an alkyl group, a cycloalkyl group, an aryl group or a heteroaryl group, g is an integer of 0 or 1, $R^{201}$ is a hydrogen atom, an alkyl group, a cycloalkyl group, an aryl group or a heteroaryl group, in a case where G is an oxygen atom or a sulfur atom, $R^{201}$ is a group other than a hydrogen atom;

(Y)

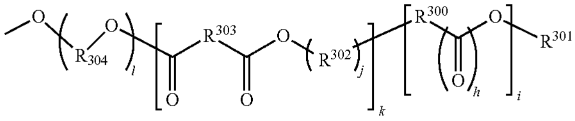

in the Formula (Y), $R^{300}$ is an alkylene group, or a silylene group having as a substituent an alkyl group or an aryl group, $R^{301}$ is an alkyl group or an aryl group, $R^{302}$, $R^{303}$ and $R^{304}$ are alkylene groups, h, j, k and l are integers of 0 or 1, i is an integer of 2 to 200, and the plural units of i may be expressed in the same or different units, or $R^1$ and $R^2$ may together form a ring that may have a heteroatom, a is an integer of 0 to 2, and b is an integer of 0 to 4, when a is 2, two $R^1$ may be different from each other, and in a case where a is 2 and two $R^1$ are present adjacent to each other, the two $R^1$ may together form a ring that may have a heteroatom, in a case where b is 2 to 4, a plurality of $R^2$ may be different from each other, and in a case where b is 2 to 4 and two $R^2$ are present adjacent to each other, the adjacent two $R^2$ may together form a ring that may have a heteroatom, $R^3$ and $R^4$ are each a bonding hand to the divalent bridging group L or a group having the bonding hand, an aryl group or a heteroaryl group, and the divalent bridging group L is a group represented by Formula (3) below:

$$—R^8—R^9—R^{10}— \quad (3)$$

in Formula (3), provided that not all of $R^8$, $R^9$ and $R^{10}$ become direct bonds at the same time, $R^8$ and $R^{10}$ are each either a direct bonding hand or a divalent aromatic ring group having 6 to 30 carbon atoms, and at least either $R^8$ or $R^{10}$ is a p-phenylene group, and $R^9$ is a direct bonding hand or a divalent organic group.

2. The photochromic cyclic compound according to claim 1, wherein n in Formula (1) is an integer of 2 or more.

3. The photochromic cyclic compound according to claim 1, wherein the naphthopyran structural group is an indenonaphthopyran structural group represented by Formula (4) below:

(4)

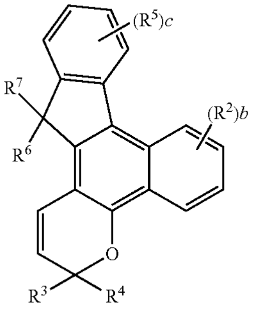

in the formula, $R^2$, $R^3$, $R^4$ and b are as described above as defined in claim 1, a structural moiety in which ($R^5$) c, $R^6$ and $R^7$ are present is a cyclic moiety formed with two $R^1$ in Formula (2), $R^5$ is a bonding hand to a divalent bridging group L, a hydroxyl group, an alkyl group, a cycloalkyl group, an alkoxy group, an amino group, a heterocyclic group, a cyano group, a halogen atom, an alkylthio group, an arylthio group, a nitro group, a formyl group, a hydroxycarbonyl group, an alkylcarbonyl group, an alkoxycarbonyl group, an aralkyl group, an aralkoxy group, an aryloxy group, an aryl group, a heteroaryl group, a thiol group, an alkoxyalkylthio group, a cycloalkylthio group, the Formula (X), or the Formula (Y), c is an integer of 0 to 4, in a case where c is 2 to 4, a plurality of $R^5$ may be different from each other, and in a case where c is 2 to 4 and two $R^5$ are present adjacent to each other, the two $R^5$ may together form a ring that may contain a heteroatom, $R^6$ and $R^7$ are each a bonding hand to the divalent bridging group L, a hydrogen atom, a hydroxyl group, an alkyl group, a cycloalkyl group, an alkoxy group, an alkoxyalkyl group, a formyl group, a hydroxycarbonyl group, an alkylcarbonyl group, an alkoxycarbonyl group, a halogen atom, an aralkyl group, an aralkoxy group, an aryloxy group, an aryl group, a heterocyclic group, the Formula (X), or the Formula (Y), or $R^6$ and $R^7$ may together form an aliphatic ring having 3 to 20 membered carbon atoms, a fused polycyclic ring in which an aromatic ring or an aromatic heterocyclic ring is fused with the aliphatic ring, a heterocyclic ring having 3 to 20 membered carbon atoms, or a fused polycyclic ring in which an aromatic ring or an aromatic heterocyclic ring is fused with the heterocyclic ring.

4. The photochromic cyclic compound according to claim 3, wherein in the indenonaphthopyran structural group represented by Formula (4), a combination of $R^6$ and $R^7$ form a ring selected from the group consisting of:

an aliphatic ring having 3 to 20 membered carbon atoms;

a fused polycyclic ring in which an aromatic ring or an aromatic heterocyclic ring is fused with the aliphatic ring;

a heterocyclic ring having 3 to 20 membered carbon atoms; or a fused polycyclic ring in which an aromatic ring or an aromatic heterocyclic ring is fused with the heterocyclic ring.

5. The photochromic cyclic compound according to claim 4, wherein in the ring formed of the combination of $R^6$ and $R^7$, the aliphatic ring having 3 to 20 carbon atoms is selected from the group consisting of a cyclopentane ring, a cyclohexane ring, a cycloheptane ring, a cyclooctane ring, a cyclononane ring, a cyclodecane ring, a cycloundecane ring, a cyclododecane ring, and a spirodicyclohexane ring.

6. The photochromic cyclic compound according to claim 5, wherein the aliphatic ring has 1 to 10 substituents, the substituent being an alkyl group having 1 to 3 carbon atoms or a cycloalkyl group having 5 to 7 carbon atoms, or the aliphatic ring is a ring with which a cycloalkyl group having 5 to 7 carbon atoms is fused.

7. The photochromic cyclic compound according to claim 1, wherein $R^3$ and $R^4$ in the Formula (2) are bonded to the divalent bridging group L.

8. The photochromic cyclic compound according to claim 1, wherein the divalent bridging group L has a molecular weight of less than 1000.

9. A photochromic curable composition comprising the photochromic cyclic compound according to claim 1 and a polymerizable compound.

10. A photochromic optical article formed by polymerizing the photochromic curable composition according to claim 9.

11. A polymer molded body in which the photochromic cyclic compound according to claim 1 is dispersed inside.

12. An optical article coated with a polymer film in which the photochromic cyclic compound according to claim 1 is dispersed.

* * * * *